United States Patent
Steiner et al.

(10) Patent No.: US 9,775,912 B2
(45) Date of Patent: *Oct. 3, 2017

(54) DESIGNED REPEAT PROTEINS BINDING TO SERUM ALBUMIN

(71) Applicant: Molecular Partners AG, Schlieren (CH)

(72) Inventors: Daniel Steiner, Zürich (CH); Hans Kaspar Binz, Birmensdorf (CH); Maya Gulotti-Georgieva, Wettswil a.A. (CH); Frieder W. Merz, Mellingen (CH); Douglas Phillips, Baden (CH); Ivo Sonderegger, Urdorf (CH)

(73) Assignee: Molecular Partners AG, Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/013,092

(22) Filed: Feb. 2, 2016

(65) Prior Publication Data
US 2016/0250341 A1 Sep. 1, 2016

Related U.S. Application Data

(63) Continuation of application No. 13/989,174, filed as application No. PCT/EP2011/071083 on Nov. 25, 2011, now Pat. No. 9,284,361.

(30) Foreign Application Priority Data
Nov. 26, 2010 (EP) .................... 10192711

(51) Int. Cl.
A61K 47/48 (2006.01)
C07K 14/47 (2006.01)
C07K 14/00 (2006.01)
C07K 16/00 (2006.01)
A61K 38/00 (2006.01)

(52) U.S. Cl.
CPC ...... A61K 47/48246 (2013.01); C07K 14/001 (2013.01); C07K 14/47 (2013.01); C07K 14/4702 (2013.01); C07K 16/00 (2013.01); A61K 38/00 (2013.01); C07K 2318/20 (2013.01); C07K 2319/00 (2013.01); C07K 2319/21 (2013.01); C07K 2319/22 (2013.01); C07K 2319/30 (2013.01); C07K 2319/31 (2013.01); C07K 2319/55 (2013.01); C07K 2319/60 (2013.01)

(58) Field of Classification Search
None
See application file for complete search history.

(56) References Cited

U.S. PATENT DOCUMENTS

| 7,417,130 B2 | 8/2008 | Stumpp et al. |
| 7,608,681 B2 | 10/2009 | Dennis et al. |
| 8,110,653 B2 | 2/2012 | Stumpp et al. |
| 8,188,223 B2 | 5/2012 | Beirnaert et al. |
| 8,642,743 B2 | 2/2014 | Herne |
| 8,710,187 B2 | 4/2014 | Binz et al. |
| 8,722,618 B2 | 5/2014 | Jacobs et al. |
| 8,846,577 B2 | 9/2014 | Steiner et al. |
| 8,901,076 B2 | 12/2014 | Binz et al. |
| 8,937,153 B2 | 1/2015 | Abrahmsen et al. |
| 9,458,211 B1 * | 10/2016 | Bakker ............... C07K 14/47 |
| 2006/0106203 A1 | 5/2006 | Winter et al. |
| 2006/0228364 A1 | 10/2006 | Dennis et al. |
| 2007/0178082 A1 | 8/2007 | Silence et al. |
| 2008/0107601 A1 | 5/2008 | Lauwereys et al. |
| 2009/0082274 A1 | 3/2009 | Stumpp et al. |
| 2010/0113339 A1 | 5/2010 | Beirnaert et al. |
| 2010/0129368 A9 | 5/2010 | Lasters et al. |
| 2010/0216187 A1 | 8/2010 | Lasters et al. |
| 2011/0207668 A1 | 8/2011 | Binz et al. |
| 2011/0224100 A1 | 9/2011 | Parmeggiani et al. |
| 2012/0142611 A1 | 6/2012 | Stumpp et al. |
| 2012/0277143 A1 | 11/2012 | Jacobs et al. |
| 2013/0116197 A1 | 5/2013 | Binz et al. |
| 2013/0244940 A1 | 9/2013 | Steiner et al. |
| 2013/0296221 A1 | 11/2013 | Binz et al. |

(Continued)

FOREIGN PATENT DOCUMENTS

| WO | WO 91/01743 | 2/1991 |
| WO | WO 2008/043821 | 4/2008 |

(Continued)

OTHER PUBLICATIONS

Amstutz et al., "Intracellular Kinase Inhibitors Selected from Combinatorial Libraries of Designed Ankyrin Repeat Proteins", The Journal of Biological Chemistry, 2005, vol. 280, No. 26., pp. 24715-24722.

Amstutz et al., "Rapid selection of specific MAP kinase-binders from designed ankyrin repeat protein libraries", Protein Engineering, Design & Selection, 2006, vol. 19, No. 5, pp. 219-229.

Binz et al. "High-affinity binders selected from designed ankyrin repeat protein libraries," Nature Biotechnology, May 2004, vol. 22, No. 5, pp. 575-582.

(Continued)

*Primary Examiner* — Christina Bradley

(74) *Attorney, Agent, or Firm* — Finnegan, Henderson, Farabow, Garrett & Dunner LLP

(57) ABSTRACT

New designed repeat proteins with binding specificity for serum albumin are described, as well as nucleic acids encoding such serum albumin binding proteins, pharmaceutical compositions comprising such proteins, the use of such proteins to modify the pharmacokinetics of therapeutic relevant polypeptides and the use of such proteins in the treatment of diseases. The repeat proteins of the invention have a substantially increased half-life in plasma compared to proteins not binding serum albumin.

21 Claims, 7 Drawing Sheets

(56) References Cited

U.S. PATENT DOCUMENTS

| | | |
|---|---|---|
| 2014/0005125 A1 | 1/2014 | Baumann |
| 2014/0206599 A1 | 7/2014 | Baumann et al. |
| 2014/0221295 A1 | 8/2014 | Binz et al. |
| 2015/0057186 A1 | 2/2015 | Steiner et al. |

FOREIGN PATENT DOCUMENTS

| | | | |
|---|---|---|---|
| WO | WO 2008/043822 | | 4/2008 |
| WO | WO 2008/096158 | | 8/2008 |
| WO | WO 2009/115919 | | 9/2009 |
| WO | WO 2010/060748 | | 6/2010 |
| WO | WO 2014/083208 A1 | * | 6/2014 |

OTHER PUBLICATIONS

Binz et al., "Crystal Structure of a Consensus-Designed Ankyrin Repeat Protein: Implications for Stability", Proteins: Structure, Function, and Bioinformatics, 2006, vol. 65, pp. 280-284.
Binz et al., "Designed Repeat Proteins-Molecules with Antibody-like Binding Properties", BIOforum Europe, Apr. 2005, pp. 34-36, GIT VERLAG GmbH & Co., KG, Darmstadt, www.gitverlag.com/go/bioint.
Binz et al., "Designing Repeat Proteins: Well-expressed, Soluble and Stable Proteins from Combinatorial Libraries of Consensus Ankyrin Repeat Proteins", J. Mol. Biol., 2003, vol. 332, pp. 489-503.
Binz et al., "Engineered proteins as specific binding reagents", Current Opinion in Biotechnology, 2005, vol. 16, pp. 459-469.
Binz et al., "Engineering novel binding proteins from nonimmunoglobulin domains", Nature Biotechnology, vol. 23, No. 10, Oct. 2005, 1257-1268.
Boersma et al., "DARPins and other repeat protein scaffolds: advances in engineering and applications" Science Direct, Current Opinion in Biotechnology, 2011, vol. 22, pp. I-9.
Dennis et al., "Albumin Binding as a General Strategy for Improving the Pharmacokineticcs of Proteins", The Journal of Biological Chemistry, 2002, vol. 277, No. 38, pp. 35035-35043.
Eggel et al., "DARPins as Bispecific Receptor Antagonists Analyzed for Immunoglobulin E Receptor Blockage", J. Mol. Biol., 2009, vol. 393, pp. 598-607.
Forrer et al. "Concensus Design of Repeat Proteins", ChemBioChem, 2004, vol. 5, pp. 183-189.
Forrer et al., "A novel strategy to design binding molecules harnessing the modular nature of repeart proteins", Federation of European Biochemical Societies, vol. 539,2003, pp. 2-6.
Ghuman et al. "Structural Basis of the Drug-binding Specificity of Human Serum Albumin" J. Mol. Bioi. (2005) 353, 38-52.
Hanes et al., "In vitro selection and evolution of functional proteins by using ribosome display", Proc. Natl. Acad. Sci, USA, 1997, vol. 94, pp. 4937-4942.
He et al., "Ribosome display: Cell-free protein display technology", Briefings in Functional Genomics and Proteomics, Jul. 2002, vol. I, No. 2, pp. 204-212.
Interlandi et al., "Characterization and Further Stabilization of Designed Ankyrin Repeart Proteins by Combining Molecular Dynamics Simulations and Experiments", J. Mol. Biol. 2008, vol. 375, pp. 837-854.
International Search Report issued Mar. 15, 2012 in International (PCT) Application No. PCT/EP2011/071083.
Kawe et al., "Isolation of Intracellular Proteinase Inhibitors Derived from Designed Ankyrin Repeat Proteins by Genetic Screening", The Journal of Biological Chemistry, 2006, 281(52), pp. I-28.
Kohl et al., "Designed to be stable: Crystal structure of a consensus ankrin repeat protein", PNAS, Feb. 18, 2003, vol. 100, No. 4, pp. 1700-1705.
Kramer et al., "Structural Determinants for Improved Stability of Designed Ankyrin Repeat Proteins with a Redesigned C-Capping Module", J. Mol. Biol., 2010, vol. 404, pp. 381-391.
Mosavi et al. "The ankyrin repeat as molecular architecture for protein recognition," Protein Science (2004), 13:1435-1448.
Sennhauser et al., "Chaperone-Assisted Crystallography with DARPins", Structure, Oct. 8, 2008, vol. 16, pp. 1443-1453.
Steiner et al. "Efficient Selection of DAR Pins with Sub-nanomolar Affinities using SRP Phage Display," J. Mol. Bioi. (2008) 382, 1211-1227.
Steiner et al. "Supplementary Material" to "Efficient Selection of DAR Pins with Sub-nanomolar Affinities using SRP Phage Display," J. Mol. Bioi. (2008) 382, 1211-1227, pp. 1-17.
Stumpp et al. "DARPins: A new generation of protein therapeutics," Drug Discovery Today, Aug. 2008, vol. 13, No. 15/16, pp. 695-701.
Stumpp et al., "DARPins: A true alternative to antibodies", Current Opinion in Drug Discovery & Development, 2007, vol. 10, No. 2, pp. 153-159.
Stumpp et al., "Designing Repeat Proteins: Modular Leucine-rich Repeat Protein Libraries Based on the Mammalian Ribonuclease Inhibitor Family", J. Mol. Biol., 2003, vol. 332, pp. 471-487.
Theurillat et al. "Designed ankyrin repeat proteins: a novel tool for testing epidermal growth factor receptor 2 expressions in breast cancer" Modem Pathology, 2010, 23(9), pp. 1-9.
Veesler et al., "Crystal Structure and Function of a DARPin Neutralizing Inhibitor of Lactococcal Phage TP901-1", The Journal of Biological Chemistry, Oct. 30, 2009, vol. 284, No. 44, pp. 30718-30726.
Zahnd et al., "A Designed Ankyrin Repeat Protein Evolved to Picomolar Affinity to Her2" J. Mol. Biol., 2007, vol. 369, 1015-1028.
Zahnd et al., "Efficient Tumor Targeting with High-Affinity Designed Ankyrin Repeat Proteins: Effects of Affinity and Molecular Size", Cancer Res, 2010, vol. 70, No. 4, pp. 1595-1605 (incl. Supplement).
Zahnd et al., "Ribosome display: selecting and evolving proteins in vitro that specifically bind to a target" Nature Methods, 2007, vol. 4, No. 3, pp. 269-279.
Zahnd et al., "Selection and Characterization of Her2 Binding-designed Ankyrin Repeat Proteins", The Journal of Biological Chemistry, 2006, vol. 281, No. 46, pp. 35167-35175.

* cited by examiner

DESIGNED REPEAT PROTEINS BINDING TO SERUM ALBUMIN

This application is a continuation of U.S. application Ser. No. 13/989,174, filed Jun. 3, 2013, which is the U.S. national stage application of International Application No. PCT/EP2011/071083, filed Nov. 25, 2011, which claims the benefit of priority of European Application No. 10192711.9 filed Nov. 26, 2010, all of which are incorporated herein by reference.

FIELD OF THE INVENTION

The present invention relates to designed repeat proteins with binding specificity for serum albumin, as well as nucleic acids encoding such serum albumin binding proteins, pharmaceutical compositions comprising such proteins, the use of such proteins to modify the pharmacokinetics of bioactive compounds and the use of such proteins in the treatment of diseases.

BACKGROUND OF THE INVENTION

There is a strong interest of the pharmaceutical industry to increase the effectiveness of bioactive compounds, such as protein therapeutics, by modulating or increasing their pharmacokinetic (PK) in vivo properties. This is especially true for bioactive compounds that are rapidly eliminated from the circulation by renal clearance. The kidney generally filters out molecules from circulation that have an apparent molecular weight below 60 kDa. One strategy to improve the pharmacokinetic properties of such small bioactive compounds is to simply increase their apparent molecular size (i.e. to increase their hydrodynamic radius), e.g. through the addition of non-proteinaceous polymer moieties such as polyethylene glycol polymers or sugar residues or the addition of proteinaceous polymer moieties such as globular proteins or unstructured polypeptides, such as those described in WO 2007/103515 and WO 2008/155134.

Other strategies harness the long circulation half-life of serum proteins, such as immunoglobulins and serum albumin. Serum albumin having a molecular weight of 67 kDa is the most abundant protein in plasma, present at about 50 mg/ml (0.6 mM), and has a serum half-life of 19 days in humans. Serum albumin helps to maintain plasma pH, contributes to colloidal blood pressure, functions as carrier of many metabolites and fatty acids, and serves as a major drug transport protein in the plasma. There are several major small molecule binding sites in albumin that have been described.

It has been shown that non-covalent association with serum albumin can extend the half-life of short lived small molecules or polypeptides (WO 1991/001743). Polypeptides that are specifically binding to serum albumin, and that thereby can extend the in vivo half-life of other molecules coupled to them, include variants of bacterial albumin binding domains (e.g. WO 2005/097202 and WO 2009/016043), small peptides (e.g. Dennis, M. S., et al., J. Biol. Chem. 277(3), 35035-43, 2002 and WO 2001/045746) and fragments of immunoglobulins (e.g. WO 2008/043822, WO 2004/003019; WO 2008/043821; WO 2006/040153; WO 2006/122787 and WO 2004/041865). WO 2008/043822 refers to other binding proteins than fragments of immunoglobulins, such as molecules based on protein A domains, tendamistat, fibronectin, lipocalin, CTLA-4, T-cell receptors, designed ankyrin repeats and PDZ domains, which might be generated to specifically bind to serum albumin. Nevertheless, WO 2008/043822 does neither disclose the selection of designed ankyrin repeat domains with binding specificity for serum albumin (SA) nor concrete repeat sequence motifs of repeat domains that specifically bind to SA. Furthermore, it was described that the in vivo half-life of polypeptides can be prolonged by their genetic fusion to serum albumin (e.g. WO 1991/001743). Such an alteration of the in vivo half-life of drugs may positively alter their pharmacokinetic (PK) and/or pharmacodynamic (PD) properties. This is a key issue in the development of new and efficient therapeutics and disease treatment methods. There is therefore a need in the art of new ways of altering PK and/or PD of bioactive compounds.

There are, beside antibodies, novel binding proteins or binding domains that can be used to specifically bind a target molecule (e.g. Binz, H. K., Amstutz, P. and Plückthun, A., Nat. Biotechnol. 23, 1257-1268, 2005). One such novel class of binding proteins or binding domains are based on designed repeat proteins or designed repeat domains (WO 2002/020565; Binz, H. K., Amstutz, P., Kohl, A., Stumpp, M. T., Briand, C., Forrer, P., Grütter, M. G., and Plückthun, A., Nat. Biotechnol. 22, 575-582, 2004; Stumpp, M. T., Binz, H. K and Amstutz, P., Drug Discov. Today 13, 695-701, 2008). WO 2002/020565 describes how large libraries of repeat proteins can be constructed and their general application. Nevertheless, WO 2002/020565 does neither disclose the selection of repeat domains with binding specificity for SA nor concrete repeat sequence motifs of repeat domains that specifically bind to SA. Furthermore, WO 2002/020565 does not suggest that repeat domains with binding specificity for SA could be used to modulate the PK or PD of other molecules. These designed repeat domains harness the modular nature of repeat proteins and possess N-terminal and C-terminal capping modules to prevent the designed repeat domains from aggregation by shielding the hydrophobic core of the domain (Forrer, P., Stumpp, M. T., Binz, H. K. and Plückthun, A., FEBS letters 539, 2-6, 2003). These capping modules were based on the capping repeats of the natural guanine-adenine-binding protein (GA-binding protein). It was shown that the thermal and thermodynamic stability of these designed ankyrin repeat domains could be further increased by improving the C-terminal capping repeat derived from the GA-binding protein (Interlandi, G., Wetzel, S. K, Settanni, G., Plückthun, A. and Caflisch, A., J. Mol. Biol. 375, 837-854, 2008; Kramer, M. A, Wetzel, S. K., Plückthun, A., Mittl, P. R. E, and Grütter, M. G., J. Mol. Biol. 404, 381-391, 2010). The authors introduced a total of eight mutations into this capping module and extended its C-terminal helix by adding three distinct amino acids. Nevertheless, the introduction of these modifications in the C-terminal capping module resulted in a tendency of unwanted dimerization of a designed repeat domain carrying this mutated C-terminal capping module. Thus, there is a need for the generation of further optimized C-terminal capping modules or C-terminal capping repeats of ankyrin repeat domains.

Targeting SA to modulate the PK and/or PD with currently available approaches is not always effective. It has even become increasingly apparent that the modulation of the PK and/or PD of molecules by hijacking SA is complex and not yet fully understood.

Overall, a need exists for improved binding proteins with specificity for SA able to improve the PK and/PD of therapeutic relevant molecules or polypeptides for treating cancer and other pathological conditions.

The technical problem underlying the present invention is identifying novel binding proteins, such as repeat domains with binding specificity to SA, able to modify the PK and/or PD of therapeutic relevant molecules for an improved treatment of cancer and other pathological conditions. The solution to this technical problem is achieved by providing the embodiments characterized in the claims.

SUMMARY OF THE INVENTION

The present invention relates to a binding protein comprising at least one ankyrin repeat domain, wherein said ankyrin repeat domain has binding specificity for a mammalian serum albumin and wherein said ankyrin repeat domain comprises an ankyrin repeat module having an amino acid sequence selected from the group consisting of SEQ ID NO:49, 50, 51 and 52 and sequences, wherein up to 9 amino acids in SEQ ID NO:49, 50, 51 and 52 are exchanged by any amino acid.

In a further embodiment, the invention relates to a binding protein comprising at least one ankyrin repeat domain, wherein said repeat domain has binding specificity for a mammalian serum albumin and wherein said ankyrin repeat domain comprises an amino acid sequence that has at least 70% amino acid sequence identity with one ankyrin repeat domain selected from the group consisting of SEQ ID NOs: 17 to 31 and 43 to 48, wherein G at position 1 and/or S at position 2 of said ankyrin repeat domain are optionally missing.

In particular, the invention relates to a binding protein as defined herein above, wherein the ankyrin repeat domain competes for binding to a mammalian serum albumin with an ankyrin repeat domain selected from the group consisting of SEQ ID NOs: 17 to 31 and 43 to 48.

Furthermore the invention relates to such a binding protein comprising a bioactive compound, in particular a binding protein comprising a bioactive compound having an at least 2-fold higher terminal plasma half-life in a mammal compared to the terminal plasma half-life of said unmodified bioactive compound.

The invention further relates to nucleic acid molecules encoding the binding proteins of the present invention, and to a pharmaceutical composition comprising one or more of the above mentioned binding proteins or nucleic acid molecules.

The invention further relates to a method of treatment of a pathological condition using the binding proteins of the invention.

BRIEF DESCRIPTION OF THE FIGURES

Elution profiles of size exclusion chromatography (SEC) runs of DARPins with specificity for xSA before (FIG. 1A), after incubation at 30 mg/ml (~2 mM) in PBS for 28 days at 40° C. (FIG. 1B) or after storage for 1 month at −80° C. (FIG. 1C) analyzed with a Superdex 200 column 5/150 (FIG. 1A or FIG. 1B) or with a superdex200 10/300GL (FIG. 1C). All samples were expressed and purified as described in Example 1. For SEC analysis samples were diluted to a concentration of 500 μM. The molecular mass standards Aprotinin (AP) 6.5 kDa, Carbonic Anhydrase (CA) 29 kDa and Conalbumin (CO) 75 kDa are indicated by arrows.

xSA, mammalian serum albumin, A, absorbance at 280 nm; t, retention time in minutes;

DARPin #19 (SEQ ID NO:19 with a His-tag (SEQ ID NO:15) fused to its N-terminus);

DARPin #20 (SEQ ID NO:20 with a His-tag (SEQ ID NO:15) fused to its N-terminus);

DARPin #21 (SEQ ID NO:21 with a His-tag (SEQ ID NO:15) fused to its N-terminus);

DARPin #22 (SEQ ID NO:22 with a His-tag (SEQ ID NO:15) fused to its N-terminus);

DARPin #27 (SEQ ID NO:27 with a His-tag (SEQ ID NO:15) fused to its N-terminus);

DARPin #28 (SEQ ID NO:28 with a His-tag (SEQ ID NO:15) fused to its N-terminus);

DARPin #29 (SEQ ID NO:29 with a His-tag (SEQ ID NO:15) fused to its N-terminus);

DARPin #30 (SEQ ID NO:30 with a His-tag (SEQ ID NO:15) fused to its N-terminus);

DARPin #43 (SEQ ID NO:43 with a His-tag (SEQ ID NO:15) fused to its N-terminus);

DARPin #44 (SEQ ID NO:44 with a His-tag (SEQ ID NO:15) fused to its N-terminus);

DARPin #45 (SEQ ID NO:45 with a His-tag (SEQ ID NO:15) fused to its N-terminus);

DARPin #46 (SEQ ID NO:46 with a His-tag (SEQ ID NO:15) fused to its N-terminus);

DARPin #47 (SEQ ID NO:47 with a His-tag (SEQ ID NO:15) fused to its N-terminus);

DARPin #48 (SEQ ID NO:48 with a His-tag (SEQ ID NO:15) fused to its N-terminus).

FIGS. 2A to 2D. Thermal Stability of Selected DARPins.

Traces from thermal denaturation of DARPins with specificity for xSA (followed by an increase of the fluorescence intensity of the dye SYPRO orange present in the buffer) in PBS at pH 7.4 (FIGS. 2A and 2B) and in MES buffer at pH 5.8 (FIGS. 2C and 2D) (250 mM (2-N-morpholino)ethanesulphonic acid pH 5.5), 150 mM NaCl, mixed with PBS pH 7.4 1 to 4 (v/v) and adjusting the pH to 5.8).

F, relative fluorescence units (RFUs), excitation at 515-535 nm, detection at 560-580 nm;

T, temperature in ° C.; Definition of DARPins see above.

Figure 3A:
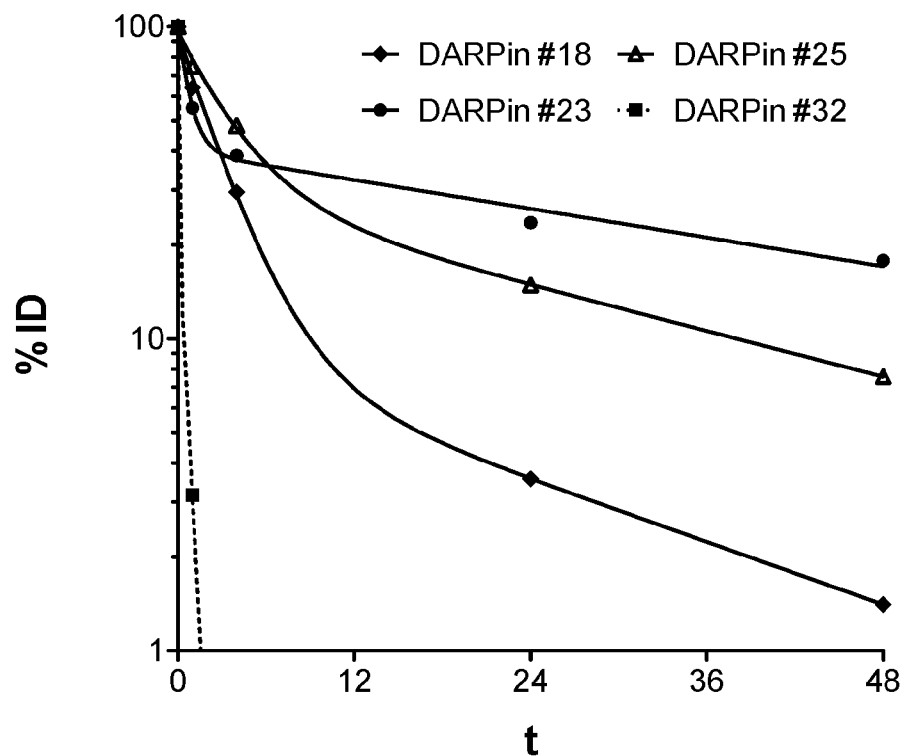
Figure 3B:
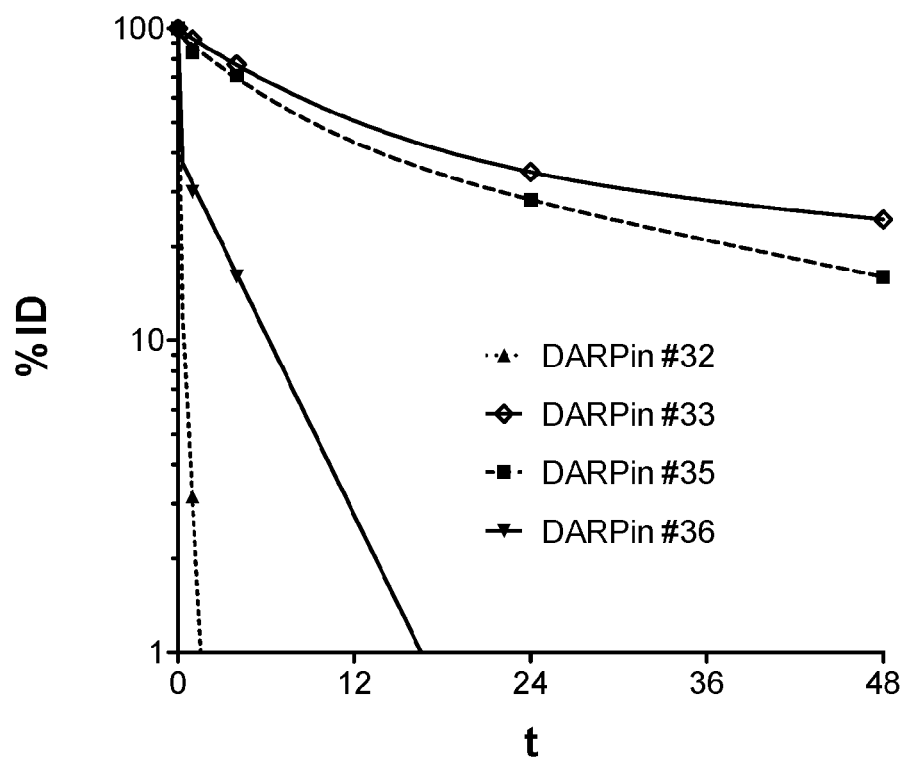

FIGS. 3A and 3B. Plasma Clearance of Selected DARPins in Mice.

The clearance from blood plasma of DARPins with specificity for MSA (mouse serum albumin) and control DARPins were assessed in mice.

(FIG. 3A) DARPins comprising just one repeat domain with binding specificity for MSA compared to DARPin #32 (see below) having no binding specificity for MSA.

(FIG. 3B) DARPins comprising two protein domains (one of which is a repeat domain with binding specificity for MSA) compared to DARPin #32 having no binding specificity for MSA.

DARPins were labeled via the His-Tag with a $^{99m}$Tc-carbonyl compound and injected intravenously in mice. The radioactivity of the blood of injected mice was measured at different time points after injection and shown as a ratio of the injected dose corrected for the radioactive decay of $^{99m}$Tc (% ID). The fitted curves show the result of non-linear regressions of the radioactivity measured at different time points—two phase decay (Graphpad Prism). Each data point indicates the average of two mice per group.

% ID, percent injected dose corrected for the radioactive decay of $^{99m}$Tc; t, time in hours;

DARPin #18 (SEQ ID NO:18 with a His-tag (SEQ ID NO:15) fused to its N-terminus);

DARPin #23 (SEQ ID NO:23 with a His-tag (SEQ ID NO:15) fused to its N-terminus);

DARPin #25 (SEQ ID NO:25 with a His-tag (SEQ ID NO:15) fused to its N-terminus);

DARPin #32 (a negative control DARPin with no binding specificity to xSA, SEQ ID NO:32 with a His-tag (SEQ ID NO:15) fused to its N-terminus);

DARPin #33 (a DARPin comprising two repeat domains, one with binding specificity for xSA, SEQ ID NO:33 with a His-tag (SEQ ID NO:15) fused to its N-terminus);

DARPin #35 (a DARPin comprising two repeat domains, one with binding specificity for xSA, SEQ ID NO:35 with a His-tag (SEQ ID NO:15) fused to its N-terminus);

DARPin #36 (a DARPin comprising two repeat domains, one with binding specificity for xSA, SEQ ID NO:36 with a His-tag (SEQ ID NO:15) fused to its N-terminus).

Figure 4A:
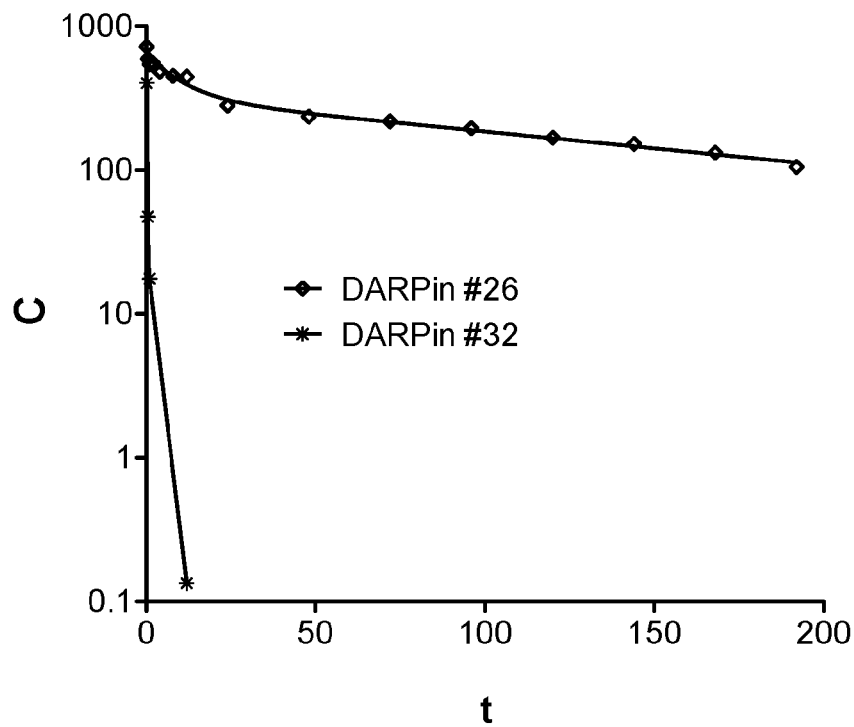
Figure 4B:
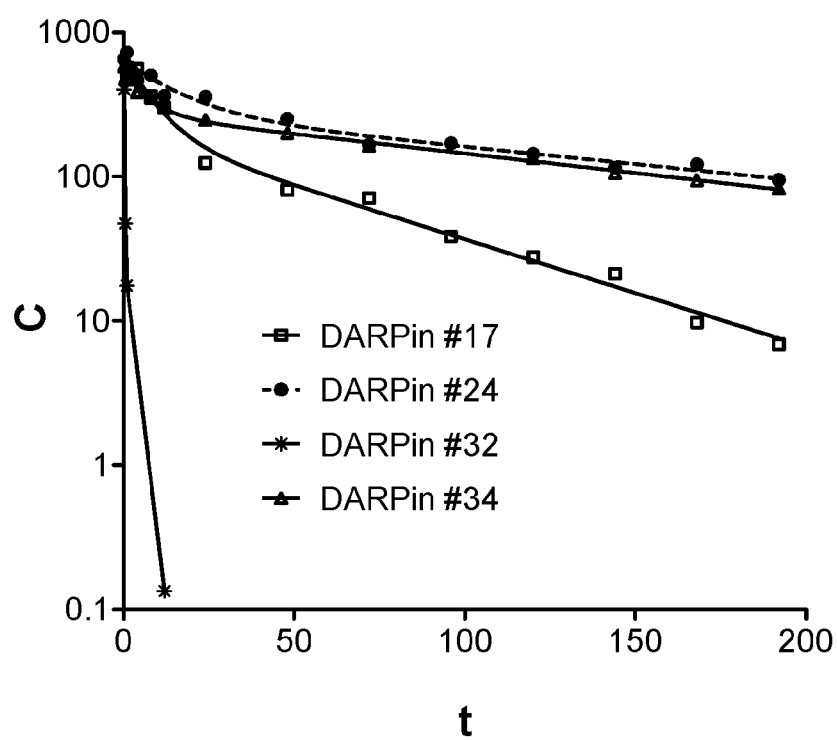

FIGS. 4A and 4B. Plasma Clearance of Selected DARPins in Cynomolgus Monkeys.

The clearance of DARPins with specificity for CSA (cynomolgus monkey serum albumin) and control DARPins from blood plasma was assessed in cynomolgus monkeys.

(FIG. 4A) DARPin #26 was compared to DARPin #32 having no binding specificity to CSA.

(FIG. 4B) DARPins #24, 34 and 17 were compared to DARPin #32 having no binding specificity to CSA. The following DARPins were intravenously injected in cynomolgus monkeys at t=0 hours at a concentration of 0.5 mg/ml (DARPin #26, DARPin #24, DARPin #17 and DARPin #32) or 1 mg/ml (DARPin #34): The concentration of the DARPins in the plasma of monkeys was measured by ELISA at different time points after injection. The curves show the result of non-linear regressions of the concentrations measured at different time points—two phase decay (Graphpad Prism). From the second phase, the terminal plasma half-life of a DARPin can be determined. Each single data point indicates the average of two independent ELISA measurements of the same serum sample.

C, DARPin concentration in nM; t, time in hours;

DARPin #17 (SEQ ID NO:17 with a His-tag (SEQ ID NO:15) fused to its N-terminus);

DARPin #24 (SEQ ID NO:24 with a His-tag (SEQ ID NO:15) fused to its N-terminus);

DARPin #26 (SEQ ID NO:26 with a His-tag (SEQ ID NO:15) fused to its N-terminus);

DARPin #32 (a negative control DARPin with no binding specificity to xSA, SEQ ID NO:32 with a His-tag (SEQ ID NO:15) fused to its N-terminus);

DARPin #34 (a DARPin comprising two repeat domains, one with binding specificity for xSA, SEQ ID NO:34 with a His-tag (SEQ ID NO:15) fused to its N-terminus).

DETAILED DESCRIPTION OF THE INVENTION

The binding domain according to the invention is specific for a mammalian serum albumin (xSA). Preferably, the binding domain according to the invention is specific for a serum albumin of mice, rat, dog, rabbit, monkey or human origin. More preferably, the binding domain according to the invention is specific for a serum albumin of human origin (HSA).

The term "protein" refers to a polypeptide, wherein at least part of the polypeptide has, or is able to acquire a defined three-dimensional arrangement by forming secondary, tertiary, or quaternary structures within and/or between its polypeptide chain(s). If a protein comprises two or more polypeptides, the individual polypeptide chains may be linked non-covalently or covalently, e.g. by a disulfide bond between two polypeptides. A part of a protein, which individually has, or is able to acquire, a defined three-dimensional arrangement by forming secondary or tertiary structures, is termed "protein domain". Such protein domains are well known to the practitioner skilled in the art.

The term "recombinant" as used in recombinant protein, recombinant protein domain, recombinant binding protein and the like, means that said polypeptides are produced by the use of recombinant DNA technologies well known by the practitioner skilled in the relevant art. For example, a recombinant DNA molecule (e.g. produced by gene synthesis) encoding a polypeptide can be cloned into a bacterial expression plasmid (e.g. pQE30, Qiagen), yeast expression plasmid or mammalian expression plasmid. When, for example, such a constructed recombinant bacterial expression plasmid is inserted into an appropriate bacteria (e.g. *Escherichia coli*), this bacteria can produce the polypeptide encoded by this recombinant DNA. The correspondingly produced polypeptide is called a recombinant polypeptide.

In the context of the present invention, the term "polypeptide" relates to a molecule consisting of one or more chains of multiple, i.e. two or more amino acids linked via peptide bonds. Preferably, a polypeptide consists of more than eight amino acids linked via peptide bonds.

The term "polypeptide tag" refers to an amino acid sequence attached to a polypeptide/protein, wherein said amino acid sequence is useful for the purification, detection, or targeting of said polypeptide/protein, or wherein said amino acid sequence improves the physicochemical behavior of the polypeptide/protein, or wherein said amino acid sequence possesses an effector function. The individual polypeptide tags, moieties and/or domains of a binding protein may be connected to each other directly or via polypeptide linkers. These polypeptide tags are all well known in the art and are fully available to the person skilled in the art. Examples of polypeptide tags are small polypeptide sequences, for example, His (e.g. the His-tag of SEQ ID NO:15), myc, FLAG, or Strep-tags or moieties such as enzymes (for example enzymes like alkaline phosphatase), which allow the detection of said polypeptide/protein, or moieties which can be used for targeting (such as immunoglobulins or fragments thereof) and/or as effector molecules.

The term "polypeptide linker" refers to an amino acid sequence, which is able to link, for example, two protein domains, a polypeptide tag and a protein domain, a protein domain and a non-polypeptide moiety such as polyethylene glycol or two sequence tags. Such additional domains, tags, non-polypeptide moieties and linkers are known to the person skilled in the relevant art. A list of example is provided in the description of the patent application WO 2002/020565. Particular examples of such linkers are glycine-serine-linkers and proline-threonine-linkers of variable lengths; preferably, said linkers have a length between 2 and 24 amino acids; more preferably, said linkers have a length between 2 and 16 amino acids. An example of a glycine-serine-linker is provided in SEQ ID NO:16.

The term "polymer moiety" refers to either a proteinaceous polymer moiety or a non-proteinaceous polymer moiety. A "proteinaceous polymer moiety" preferably is a polypeptide that does not form a stable tertiary structure while not forming more than 10%, preferably, not more than 5%; also preferred, not more than 2%; even more preferably, not more than 1%; and most preferably, no detectable amounts, as determined by size exclusion chromatography (SEC) of oligomers or aggregates when stored at a concentration of about 0.1 mM in phosphate buffered saline (PBS) at room temperature (RT) for one month. Such proteinaceous polymer moieties run at an apparent molecular weight in SEC that is higher than their effective molecular weight when using globular proteins as molecular weight standards for the SEC. Preferably, the apparent molecular weight of said proteinaceous polymer moieties determined by SEC is 1.5×, 2× or 2.5× higher than their effective molecular weight calculated from their amino acid sequence. Also preferably, the apparent molecular weights of said non-proteinaceous polymer moieties determined by SEC is 2×, 4× or 8× higher than their effective molecular weight calculated from their molecular composition. Preferably, more than 50%, 70% or even 90% of the amino acids of said proteinaceous polymer moiety do not form stable secondary structures at a concentration of about 0.1 mM in PBS at RT as determined by Circular Dichroism (CD) measurements. Most preferably, said proteinaceous polymer shows a typical near UV CD-spectra of a random coil conformation. Such CD analyses are well known to the person skilled in the art. Also preferable are proteinaceous polymer moieties that consist of more than 50, preferably more than 100, 200, 300, 400, 500, 600, 700, or most preferably more than 800 amino acids. Examples of proteinaceous polymer moieties are XTEN® (a registered trademark of Amunix; WO 2007/103515) polypeptides, or polypeptides comprising proline, alanine and serine residues as described in WO 2008/155134. Such proteinaceous polymer moieties can be covalently attached to, for example, a binding domain of the invention by the generation of genetic fusion polypeptides using standard DNA cloning technologies, followed by their standard expression and purification.

A polymer moiety of the invention may vary widely in molecular weight (i.e. from about 1 kDa to about 150 kDa). Preferably, the polymer moiety has a molecular weight of at least 2, more preferably at least 5, 10, 20, 30, 50, 70, or most preferably at least 100 kDa. Preferably, said polymer moiety is connected by a polypeptide linker to a binding domain.

Examples of non-proteinaceous polymer moieties are hydroxyethyl starch (HES), polyethylene glycol (PEG), polypropylene glycol, or polyoxyalkylene. The term "PEGylated" means that a PEG moiety is covalently attached to, for example, a polypeptide of the invention.

In a specific embodiment, a PEG moiety or any other non-proteinaceous polymer can, e.g., be coupled to a cysteine thiol via a maleimide linker with the cysteine being coupled via a peptide linker to the N- or C-terminus of a binding domain as described herein.

The term "binding protein" refers to a protein comprising one or more binding domains, one or more bioactive compounds and one or more polymer moieties as further explained below. Preferably, said binding protein comprises up to four binding domains. More preferably, said binding protein comprises up to two binding domains. Most preferably, said binding protein comprises only one binding domain. Furthermore, any such binding protein may comprise additional protein domains that are not binding domains, multimerization moieties, polypeptide tags, polypeptide linkers and/or a single Cys residue. Examples of multimerization moieties are immunoglobulin heavy chain constant regions which pair to provide functional immunoglobulin Fc domains, and leucine zippers or polypeptides comprising a free thiol which forms an intermolecular disulfide bond between two such polypeptides. The single Cys residue may be used for conjugating other moieties to the polypeptide, for example, by using the maleimide chemistry well known to the person skilled in the art. Preferably, said binding protein is a recombinant binding protein. Also preferably, the binding domains of binding protein possess different target specificities.

The term "binding domain" means a protein domain exhibiting the same "fold" (three-dimensional arrangement) as a protein scaffold and having a predetermined property, as defined below. Such a binding domain may be obtained by rational, or most commonly, combinatorial protein engineering techniques, skills which are known in the art (Binz et al., 2005, loc. cit.). For example, a binding domain having a predetermined property can be obtained by a method comprising the steps of (a) providing a diverse collection of protein domains exhibiting the same fold as a protein scaffold as defined further below; and (b) screening said diverse collection and/or selecting from said diverse collection to obtain at least one protein domain having said predetermined property. The diverse collection of protein domains may be provided by several methods in accordance with the screening and/or selection system being used, and may comprise the use of methods well known to the person skilled in the art, such as phage display or ribosome display. Preferably, said binding domain is a recombinant binding domain.

The term "protein scaffold" means a protein with exposed surface areas in which amino acid insertions, substitutions or deletions are highly tolerable. Examples of protein scaffolds that can be used to generate binding domains of the present invention are antibodies or fragments thereof such as single-chain Fv or Fab fragments, protein A from *Staphylococcus aureus*, the bilin binding protein from *Pieris brassicae* or other lipocalins, ankyrin repeat proteins or other repeat proteins, and human fibronectin. Protein scaffolds are known to the person skilled in the art (Binz et al., 2005, loc. cit.; Binz et al., 2004, loc. cit.).

The term "predetermined property" refers to a property such as binding to a target, blocking of a target, activation of a target-mediated reaction, enzymatic activity, and related further properties. Depending on the type of desired property, one of ordinary skill will be able to identify format and necessary steps for performing screening and/or selection of a binding domain with the desired property. Preferably, said predetermined property is binding to a target.

The definitions hereinafter for repeat proteins are based on those in patent application WO 2002/020565. Patent application WO 2002/020565 further contains a general description of repeat protein features, techniques and applications.

The term "repeat proteins" refers to a protein comprising one or more repeat domains. Preferably, each of said repeat proteins comprises up to four repeat domains. More preferably, each of said repeat proteins comprises up to two repeat domains. Most preferably, each of the repeat proteins comprises only one repeat domain. Furthermore, said repeat protein may comprise additional non-repeat protein domains, polypeptide tags and/or polypeptide linkers.

The term "repeat domain" refers to a protein domain comprising two or more consecutive repeat units (modules) as structural units, wherein said structural units have the same fold, and stack tightly to create, for example, a superhelical structure having a joint hydrophobic core. Preferably, a repeat domain further comprises an N-terminal and/or a C-terminal capping unit (or module). Even more preferably, said N-terminal and/or C-terminal capping units (or modules) are capping repeats.

The term "designed repeat protein" and "designed repeat domain" refer to a repeat protein or repeat domain, respectively, obtained as the result of the inventive procedure explained in patent application WO 2002/020565. Designed repeat proteins and designed repeat domains are synthetic and not from nature. They are man-made proteins or domains, respectively, obtained by expression of correspondingly designed nucleic acids. Preferably, the expression is done in eukaryotic or prokaryotic cells, such as bacterial cells, or by using a cell-free in vitro expression system. Accordingly, a designed ankyrin repeat protein (i.e. a DARPin) corresponds to a binding protein of the invention comprising at least one ankyrin repeat domain.

The term "structural unit" refers to a locally ordered part of a polypeptide, formed by three-dimensional interactions between two or more segments of secondary structure that are near one another along the polypeptide chain. Such a structural unit exhibits a structural motif. The term "structural motif" refers to a three-dimensional arrangement of secondary structure elements present in at least one structural unit. Structural motifs are well known to the person skilled in the art. Structural units alone are not able to acquire a defined three-dimensional arrangement; however, their consecutive arrangement, for example as repeat modules in a repeat domain, leads to a mutual stabilization of neighboring units resulting in a superhelical structure.

The term "repeat unit" refers to amino acid sequences comprising repeat sequence motifs of one or more naturally occurring repeat proteins, wherein said "repeat units" are found in multiple copies, and which exhibit a defined folding topology common to all said motifs determining the fold of the protein. Such repeat units correspond to the "repeating structural units (repeats)" of repeat proteins as described by Forrer et al., 2003, loc. cit. or the "consecutive homologous structural units (repeats)" of repeat proteins as described by Binz et al, 2004, loc. cit. Such repeat units comprise framework residues and interaction residues. Examples of such repeat units are armadillo repeat units, leucine-rich repeat units, ankyrin repeat units, tetratricopeptide repeat units, HEAT repeat units, and leucine-rich variant repeat units. Naturally occurring proteins containing two or more such repeat units are referred to as "naturally occurring repeat proteins". The amino acid sequences of the individual repeat units of a repeat protein may have a significant number of mutations, substitutions, additions and/or deletions when compared to each other, while still substantially retaining the general pattern, or motif, of the repeat units.

The term "ankyrin repeat unit" shall mean a repeat unit, which is an ankyrin repeat as described, for example, by Forrer et al., 2003, loc. cit. Ankyrin repeats are well known to the person skilled in the art.

The term "framework residues" relates to amino acid residues of the repeat units, or the corresponding amino acid residues of the repeat modules, which contribute to the folding topology, i.e. which contribute to the fold of said repeat unit (or module) or which contribute to the interaction with a neighboring unit (or module). Such contribution might be the interaction with other residues in the repeat unit (or module), or the influence on the polypeptide backbone conformation as found in α-helices or β-sheets, or amino acid stretches forming linear polypeptides or loops.

The term "target interaction residues" refers to amino acid residues of the repeat units, or the corresponding amino acid residues of the repeat modules, which contribute to the interaction with target substances. Such contribution might be the direct interaction with the target substances, or the influence on other directly interacting residues, e.g. by stabilizing the conformation of the polypeptide of a repeat unit (or module) to allow or enhance the interaction of directly interacting residues with said target. Such framework and target interaction residues may be identified by analysis of the structural data obtained by physicochemical methods, such as X-ray crystallography, NMR and/or CD spectroscopy, or by comparison with known and related structural information well known to practitioners in structural biology and/or bioinformatics.

Preferably, the repeat units used for the deduction of a repeat sequence motif are homologous repeat units, wherein the repeat units comprise the same structural motif and wherein more than 70% of the framework residues of said repeat units are homologous to each other. Preferably, more than 80% of the framework residues of said repeat units are homologous. Most preferably, more than 90% of the framework residues of said repeat units are homologous. Computer programs to determine the percentage of homology between polypeptides, such as Fasta, Blast or Gap, are known to the person skilled in the art. Further preferably, the repeat units used for the deduction of a repeat sequence motif are homologous repeat units obtained from repeat domains selected on a target, for example as described in Example 1 and having the same target specificity.

The term "repeat sequence motif" refers to an amino acid sequence, which is deduced from one or more repeat units or repeat modules. Preferably, said repeat units or repeat modules are from repeat domains having binding specificity for the same target. Such repeat sequence motifs comprise framework residue positions and target interaction residue positions. Said framework residue positions correspond to the positions of framework residues of the repeat units (or modules). Likewise, said target interaction residue positions correspond to the positions of target interaction residues of the repeat units (or modules). Repeat sequence motifs comprise fixed positions and randomized positions. The term "fixed position" refers to an amino acid position in a repeat sequence motif, wherein said position is set to a particular amino acid. Most often, such fixed positions correspond to the positions of framework residues and/or the positions of target interaction residues that are specific for a certain target. The term "randomized position" refers to an amino acid position in a repeat sequence motif, wherein two or more amino acids are allowed at said amino acid position, for example, wherein any of the usual twenty naturally occurring amino acids are allowed, or wherein most of the twenty naturally occurring amino acids are allowed, such as amino acids other than cysteine, or amino acids other than glycine, cysteine and proline. Most often, such randomized positions correspond to the positions of target interaction residues. However, some positions of framework residues may also be randomized.

The term "folding topology" refers to the tertiary structure of said repeat units or repeat modules. The folding topology will be determined by stretches of amino acids forming at least parts of α-helices or δ-sheets, or amino acid stretches forming linear polypeptides or loops, or any combination of α-helices, δ-sheets and/or linear polypeptides/loops.

The term "consecutive" refers to an arrangement, wherein the repeat units or repeat modules are arranged in tandem. In designed repeat proteins, there are at least 2, usually about 2 to 6, in particular at least about 6, frequently 20 or more repeat units (or modules). In most cases, repeat units (or modules) of a repeat domain will exhibit a high degree of sequence identity (same amino acid residues at corresponding positions) or sequence similarity (amino acid residues being different, but having similar physicochemical properties), and some of the amino acid residues might be key residues being strongly conserved. However, a high degree of sequence variability by amino acid insertions and/or deletions, and/or substitutions between the different repeat units (or modules) of a repeat domain may be possible as long as the common folding topology of the repeat units (or modules) is maintained.

Methods for directly determining the folding topology of repeat proteins by physicochemical means such as X-ray crystallography, NMR or CD spectroscopy, are well known to the practitioner skilled in the art. Methods for identifying and determining repeat units or repeat sequence motifs or for identifying families of related proteins comprising such repeat units or motifs, such as homology searches (BLAST etc.), are well established in the field of bioinformatics, and are well known to the practitioner in the art. The step of refining an initial repeat sequence motif may comprise an iterative process.

The term "repeat modules" refers to the repeated amino acid sequences of the designed repeat domains, which are originally derived from the repeat units of naturally occurring repeat proteins. Each repeat module comprised in a repeat domain is derived from one or more repeat units of the family or subfamily of naturally occurring repeat proteins, e.g. the family of armadillo repeat proteins or ankyrin repeat proteins.

"Repeat modules" may comprise positions with amino acid residues present in all copies of corresponding repeat modules ("fixed positions") and positions with differing or "randomized" amino acid residues ("randomized positions").

A binding protein according to the invention comprises at least one ankyrin repeat domain, wherein said repeat domain has binding specificity for mammalian serum albumin (xSA).

The term "has binding specificity for a target", "specifically binding to a target" or "target specificity" and the like means that a binding protein or binding domain binds in PBS to a target with a lower dissociation constant than to an unrelated protein such as the *E. coli* maltose binding protein (MBP). Preferably, the dissociation constant in PBS for the target is at least 10, more preferably $10^2$, even more preferably $10^3$, or most preferably $10^4$ times lower than the corresponding dissociation constant for MBP.

The binding protein of the invention is not an antibody or a fragment thereof, such as Fab or scFv fragments. Antibodies and fragments thereof are well known to the person skilled in the art.

Also, the binding domain of the invention does not comprise an immunoglobulin fold as present in antibodies and/or the fibronectin type III domain. An immunoglobulin fold is a common all-β protein fold that consists of a two-layer sandwich of about 7 anti-parallel β-strands arranged in two β-sheets. Immunoglobulin folds are well known to the person skilled in the art. For example, such binding domains comprising an immunoglobulin fold are described in WO 2007/080392 or WO 2008/097497.

In particular the invention relates to a binding protein comprising at least one ankyrin repeat domain, wherein said ankyrin repeat domain has binding specificity for a mammalian serum albumin and wherein said ankyrin repeat domain comprises an ankyrin repeat module having an amino acid sequence selected from the group consisting of SEQ ID NO:49, 50, 51 and 52 and sequences, wherein up to 9 amino acids in SEQ ID NO:49, 50, 51 and 52 are exchanged by any amino acid.

Preferably, up to 8 amino acids in SEQ ID NO:49, 50, 51 and 52 are exchanged by other amino acid, more preferably up to 7 amino acids, more preferably up to 6 amino acids, more preferably up to 5 amino acids, even more preferably up to 4 amino acids, more preferably up to 3 amino acids, more preferably up to 2 amino acids, more preferably up to 1 amino acid, and most preferably no amino acid in SEQ ID NO:49, 50, 51 and 52 is exchanged.

Preferably, when amino acids are exchanged in SEQ ID NO:49, 50, 51 and 52, these amino acids are selected from the group consisting of A, D, E, F, H, I, K, L, M, N, Q, R, S, T, V, W and Y; more preferably from the group consisting of A, D, E, H, I, K, L, Q, R, S, T, V, and Y. Also preferably, the replacement of amino acids is by a homologous amino acid; i.e. an amino acid is exchanged by an amino acid having a side chain with similar biophysical properties. For example, the negative charged amino acid D may be replaced by the negative charged amino acid E, or a hydrophobic amino acid such as L may be replaced by A, I or V. The replacement of an amino acid by a homologous amino acid is well known to the person skilled in the art.

A preferred binding protein comprises at least one ankyrin repeat domain, wherein said repeat domain binds xSA with a dissociation constant (Kd) in PBS below $10^{-4}$M. Preferably, said repeat domain binds xSA with a Kd in PBS below $10^{-4}$M, more preferably below $10^{-5}$M, $10^{-6}$M, $10^{-7}$M, or most preferably $10^{-8}$M.

Methods to determine dissociation constants of protein-protein interactions, such as surface plasmon resonance (SPR) based technologies (e.g. SPR equilibrium analysis) or isothermal titration calorimetry (ITC), are well known to the person skilled in the art. The measured Kd values of a particular protein-protein interaction can vary if measured under different conditions (e.g., salt concentration, pH). Thus, measurements of Kd values are preferably made with standardized solutions of protein and a standardized buffer, such as PBS.

Binding proteins comprising an ankyrin repeat domain binding xSA with a Kd in PBS below $10^{-4}$M are shown in the Examples.

An ankyrin repeat domain of a binding protein of the invention binds xSA. Preferred is a binding protein comprising an ankyrin repeat domain that binds human serum albumin (HSA).

Further preferred is a binding domain comprising between 70 and 300 amino acids, in particular between 100 and 200 amino acids.

Further preferred is a binding protein or binding domain devoid of a free Cys residue. A "free Cys residue" is not involved in the formation of a disulfide bond. Even more preferred is a binding protein or binding domain free of any Cys residue.

A binding domain of the invention is an ankyrin repeat domain or a designed ankyrin repeat domain (Binz et al., 2004, loc. cit.), preferably as described in WO 2002/020565. Examples of designed ankyrin repeat domains are shown in the Examples.

In a further embodiment, the invention relates to a binding protein comprising at least one ankyrin repeat domain, wherein said repeat domain has binding specificity for a mammalian serum albumin and wherein said ankyrin repeat domain comprises an amino acid sequence that has at least 70% amino acid sequence identity with one ankyrin repeat domain selected from the group consisting of SEQ ID NOs: 17 to 31 and 43 to 48, wherein G at position 1 and/or S at position 2 of said ankyrin repeat domain are optionally missing.

Preferably, such an ankyrin repeat domain in a binding protein of the invention comprises an amino acid sequence that has at least 70% amino acid sequence identity with one ankyrin repeat domain selected from the group consisting of SEQ ID NO: 21, 27 and 46; preferably 27 and 46. As defined above, said ankyrin repeat domain binds xSA with a dissociation constant (Kd) in PBS below $10^{-4}$M. Preferably, said repeat domain binds xSA with a Kd in PBS below $10^{-4}$M, more preferably below $10^{-5}$M, $10^{-6}$M, $10^{-7}$M, or most preferably $10^{-8}$M.

Preferably, such an ankyrin repeat domain in a binding protein of the invention comprises an amino acid sequence with at least 70% amino acid sequence identity with "randomized repeat units" or "randomized positions" in an ankyrin repeat domain selected from the group consisting of SEQ ID NOs: 17 to 31 and 43 to 48.

Preferably, instead of 70% amino acid sequence identity, such an ankyrin repeat domain in a binding protein of the invention comprises an amino acid sequence with at least 75%, more preferably at least 80%, more preferably at least 85%, more preferably at least 90%, or most preferred at least 95% amino acid sequence identity.

In a particular embodiment, the binding protein with binding specificity for mammalian serum albumin defined by replacement of up to 9 amino acids in ankyrin repeat modules of SEQ ID NO:49, 50, 51 and 52, or defined by at least 70% amino acid sequence identity with one ankyrin repeat domain selected from the group consisting of SEQ ID NOs: 17 to 31 and 43 to 48, has at least a 5-fold higher terminal plasma half-life in a mammal compared to a corresponding binding protein not binding to mammalian serum albumin, for example the ankyrin repeat domain of SEQ ID NO:32. In such a preferred binding protein the minimum terminal plasma half-life in human is at least 1 day, more preferably at least 3 days, even more preferably at least 5 days.

In a further embodiment, the invention relates to a binding protein, wherein said ankyrin repeat domain comprises a repeat module with the ankyrin repeat sequence motif (SEQ ID NO: 53)
$X_1DX_2X_3X_4X_5TPLHLAAX_6X_7GHLX_8IVEVLLKX_9GADVNA$ wherein $X_1$, $X_2$, $X_3$, $X_4$, $X_5$, $X_6$, $X_7$, $X_8$ and $X_9$, represent, independently of each other, an amino acid residue selected from the group consisting of A, D, E, F, H, I, K, L, M, N, Q, R, S, T, V, W and Y;

preferably wherein $X_1$ represents an amino acid residue selected from the group consisting of A, D, M, F, S, I, T, N, Y and K; more preferably of K and A;

$X_2$ represents an amino acid residue selected from the group consisting of E, K, D, F, M, N, I and Y; more preferably of I, E and Y;

$X_3$ represents an amino acid residue selected from the group consisting of W, R, N, T, H, K, A and F; more preferably of W, R and F;

$X_4$ represents an amino acid residue selected from the group consisting of G and S;

$X_5$ represents an amino acid residue selected from the group consisting of N, T and H;

$X_6$ represents an amino acid residue selected from the group consisting of N, V and R;

$X_7$ represents an amino acid residue selected from the group consisting of E, Y, N, D, H, S, A, Q, T and G; more preferably of E, Y and N;

$X_8$ represents an amino acid residue selected from the group consisting of E and K;

$X_9$ represents an amino acid residue selected from the group consisting of S, A, Y, H and N; more preferably of Y and H; and wherein optionally up to 5 amino acids in other than in positions denoted with X in SEQ ID NO:53 are exchanged by any amino acid.

In particular, the invention relates to a binding protein, wherein the ankyrin repeat domain comprises a repeat module with the ankyrin repeat sequence motif (SEQ ID NO: 10)
$X_1DX_2X_3GX_4TPLHLAAX_5X_6GHLEIVEVLLKX_7GADVNA$ wherein $X_1$ represents an amino acid residue selected from the group consisting of A, D, M, F, S, I, T, N, Y, and K; preferably of K and A;

$X_2$ represents an amino acid residue selected from the group consisting of E, K, D, F, M, N, I and Y; preferably of I, E and Y;

$X_3$ represents an amino acid residue selected from the group consisting of W, R, N, T, H, K, A and F; preferably of W, R and F;

$X_4$ represents an amino acid residue selected from the group consisting of N, T and H;

$X_5$ represents an amino acid residue selected from the group consisting of N, V and R;

$X_6$ represents an amino acid residue selected from the group consisting of E, Y, N, D, H, S, A, Q, T and G; preferably of E, Y and N;

$X_7$ represent an amino acid residue selected from the group consisting of S, A, Y, H and N; preferably of Y and H; and wherein optionally up to 5 amino acids in other than in positions denoted with X in SEQ ID NO:10 are exchanged by any amino acid.

In a further embodiment, the invention relates to a binding protein, wherein the ankyrin repeat domain comprises a repeat module with the ankyrin repeat sequence motif (SEQ ID NO: 11)
$X_1DYFX_2HTPLHLAARX_3X_4HLX_5IVEVLLKX_6GADVNA$ wherein $X_1$ represents an amino acid residue selected from the group consisting of D, K and A; preferably K and A;

$X_2$ represents an amino acid residue selected from the group consisting of D, G and S; preferably G and S;

$X_3$ represents an amino acid residue selected from the group consisting of E, N, D, H, S, A, Q, T and G; preferably Q, D and N; more preferably of Q and N;

$X_4$ represents an amino acid residue selected from the group consisting of G and D;

$X_5$ represents an amino acid residue selected from the group consisting of E, K and G; preferably E and K;

$X_6$ represents an amino acid residue selected from the group consisting of H, Y, A and N; preferably H, A and Y; more preferably of A and Y; and wherein optionally up to 5 amino acids in other than in positions denoted with X in SEQ ID NO:11 are exchanged by any amino acid.

In yet another embodiment, the invention relates to a binding protein, wherein the ankyrin repeat domain comprises a repeat module with the ankyrin repeat sequence motif (SEQ ID NO: 54)
$X_1DFX_2GX_3TPLHLAAX_4X_5GHLEIVEVLLKX_6GADVNA$ wherein X₁ represents an amino acid residue selected from the group consisting of F, S, L and K; preferably of S and K;

X₂ represents an amino acid residue selected from the group consisting of V and A;

X₃ represents an amino acid residue selected from the group consisting of R and K;

X₄ represents an amino acid residue selected from the group consisting S and N;

X₅ represents an amino acid residue selected from the group consisting of N, D, Q, S, A, T and E; preferably D and Q;

X₆ represents an amino acid residue selected from the group consisting of A, H, Y, S and N; preferably of A and H; and wherein optionally up to 5 amino acids in other than in positions denoted with X in SEQ ID NO:54 are exchanged by any amino acid.

In particular, the invention relates to a binding protein, wherein the ankyrin repeat domain comprises a repeat module with the ankyrin repeat sequence motif (SEQ ID NO: 12)
X₁DFX₂GX₃TPLHLAAX₄DGHLEIVEVLLKX₅GADVNA wherein X₁ represents an amino acid residue selected from the group consisting of F, S, L and K; preferably S and K;

X₂ represents an amino acid residue selected from the group consisting of V and A;

X₃ represents an amino acid residue selected from the group consisting of R and K;

X₄ represents an amino acid residue selected from the group consisting of S and N;

X₅ represents an amino acid residue selected from the group consisting of A, H, Y, S and N; preferably A and H; and wherein optionally up to 5 amino acids in other than in positions denoted with X in SEQ ID NO:12 are exchanged by any amino acid.

Preferred is a binding protein, wherein said ankyrin repeat domain comprises a repeat module with the ankyrin repeat sequence motif of SEQ ID NO:12, preceded by a repeat module with the ankyrin repeat sequence motif of SEQ ID NO:11.

In yet another embodiment, the invention relates to a binding protein, wherein the ankyrin repeat domain comprises a repeat module with the ankyrin repeat sequence motif (SEQ ID NO: 13)
X₁DX₂X₃GTTPLHLAAVYGHLEX₄VEVLLKX₅GADVNA wherein X₁ represents an amino acid residue selected from the group consisting of K, A, D, M, F, S, I, T, N, and Y; preferably K and A;

X₂ represents an amino acid residue selected from the group consisting of E, K, D, F, M, N and Y; preferably E, D and Y;

X₃ represents an amino acid residue selected from the group consisting of R, N, T, H, K, A and F; preferably R and F;

X₄ represents an amino acid residue selected from the group consisting of I and M;

X₅ represents an amino acid residue selected from the group consisting of H, Y, K, A and N; preferably K and A; and wherein optionally up to 5 amino acids in other than in positions denoted with X in SEQ ID NO:13 are exchanged by any amino acid.

In yet another embodiment, the invention relates to a binding protein, wherein the ankyrin repeat domain comprises a repeat module with the ankyrin repeat sequence motif (SEQ ID NO: 14)
X₁NETGYTPLHLADSSGHX₂EIVEVLLKX₃X₄X₅DX₆NA wherein X₁ represents an amino acid residue selected from the group consisting of Q and K;

X₂ represents an amino acid residue selected from the group consisting of L and P;

X₃ represents an amino acid residue selected from the group consisting of H, N, Y and A; preferably H and A;

X₄ represents an amino acid residue selected from the group consisting of G and S;

X₅ represents an amino acid residue selected from the group consisting of A, V, T and S; preferably S and A;

X₆ represents an amino acid residue selected from the group consisting of V and F; and wherein optionally up to 5 amino acids in other than in positions denoted with X in SEQ ID NO:14 are exchanged by any amino acid.

Preferred is a binding protein, wherein said ankyrin repeat domain comprises a repeat module with the ankyrin repeat sequence motif of SEQ ID NO:14, preceded by a repeat module with the ankyrin repeat sequence motif of SEQ ID NO:13.

The term "capping module" refers to a polypeptide fused to the N- or C-terminal repeat module of a repeat domain, wherein said capping module forms tight tertiary interactions (i.e. tertiary structure interactions) with said repeat module thereby providing a cap that shields the hydrophobic core of said repeat module at the side not in contact with the consecutive repeat module from the solvent. Said N- and/or C-terminal capping module may be, or may be derived from, a capping unit or other structural unit found in a naturally occurring repeat protein adjacent to a repeat unit. The term "capping unit" refers to a naturally occurring folded polypeptide, wherein said polypeptide defines a particular structural unit which is N- or C-terminally fused to a repeat unit, wherein said polypeptide forms tight tertiary structure interactions with said repeat unit thereby providing a cap that shields the hydrophobic core of said repeat unit at one side from the solvent. Preferably, capping modules or capping units are capping repeats. The term "capping repeat" refers to capping module or capping unit having a similar or the same fold as said adjacent repeat unit (or module) and/or sequence similarities to said adjacent repeat unit (or module). Capping modules and capping repeats are described in WO 2002/020565 and by Interlandi et al., 2008 (loc. cit.). For example, WO 2002/020565 describes the N-terminal capping module (i.e. a capping repeat) having the amino acid sequence GSDLGKKLLEAARAGQDDEVRILMANGADVNA (SEQ ID NO:1) and the C-terminal capping module (i.e. a capping repeat) having the amino acid sequence QDKFGKTAFDISIDNGNEDLAEILQKLN (SEQ ID NO:2).

Interlandi et al., 2008 (loc. cit.) describe the C-terminal capping modules having the amino acid sequences QDKFGKTPFDLAIREGHEDIAEVLQKAA (SEQ ID NO:3) and QDKFGKTPFDLAIDNGNEDIAEVLQKAA (SEQ ID NO:4).

For example, the N-terminal capping module of SEQ ID NO:17 is encoded by the amino acids from position 1 to 32 and the C-terminal capping module of SEQ ID NO:17 is encoded by the amino acids form position 99 to 126.

A preferred N-terminal capping module comprises the sequence motif $$X_1LX_2KKLLEAARAGQDDEVRILX_3AX_4GADVNA \quad \text{(SEQ ID NO: 5)}$$

wherein $X_1$ represents an amino acid residue G, A or D;
wherein $X_2$ represents an amino acid residue G or D;
wherein $X_3$ represents an amino acid residue L, V, I, A or M; preferably, L or M; and
wherein $X_4$ represents an amino acid residue A, H, Y, K, R or N; preferably, A or N.

Further preferred is any such N-terminal capping module comprising an N-terminal capping repeat, wherein one or more of the amino acids residues in said capping repeat are replaced by an amino acid residue found at the corresponding position on alignment of a corresponding capping unit or repeat unit.

A preferred C-terminal capping module comprises the sequence motif $$X_1DKX_2GKTX_3X_4DX_5X_6X_7DX_8GX_9EDX_{10}AEX_{11}LQKAA \quad \text{(SEQ ID NO: 6)}$$

wherein $X_1$ represents an amino acid residue Q or K;
wherein $X_2$ represents an amino acid residue A, S or F; preferably, S or F;
wherein $X_3$ represents an amino acid residue A or P;
wherein $X_4$ represents an amino acid residue A or F;
wherein $X_5$ represents an amino acid residue I or L;
wherein $X_6$ represents an amino acid residue S or A;
wherein $X_7$ represents an amino acid residue I or A;
wherein $X_8$ represents an amino acid residue A, E or N; preferably, A or N;
wherein $X_9$ represents an amino acid residue N or H;
wherein $X_{10}$ represents an amino acid residue L or I;
wherein $X_{11}$ represents an amino acid residue I or V; and
wherein $X_2$ does not represent F if $X_4$ represents F and $X_7$ represents I and $X_8$ represents N or E.

A further preferred C-terminal capping module comprises the sequence motif $$X_1DKX_2GKTX_3ADX_4X_5X_6DX_7GX_8EDX_9AEX_{10}LQKAA \quad \text{(SEQ ID NO: 7)}$$

wherein $X_1$ represents an amino acid residue Q or K;
wherein $X_2$ represents an amino acid residue A, S or F; preferably, S or F;
wherein $X_3$ represents an amino acid residue A or P;
wherein $X_4$ represents an amino acid residue I or L;
wherein $X_5$ represents an amino acid residue S or A;
wherein $X_6$ represents an amino acid residue I or A;
wherein $X_7$ represents an amino acid residue A, E or N; preferably, A or N;
wherein $X_8$ represents an amino acid residue N or H;
wherein $X_9$ represents an amino acid residue L or I; and
wherein $X_{10}$ represents an amino acid residue I or V.

A further preferred C-terminal capping module comprises the sequence motif $$X_1DKX_2GKTX_3ADX_4X_5ADX_6GX_7EDX_8AEX_9LQKAA \quad \text{(SEQ ID NO: 8)}$$

wherein $X_1$ represents an amino acid residue Q or K;
wherein $X_2$ represents an amino acid residue A, S or F; preferably, S or F;
wherein $X_3$ represents an amino acid residue A or P;
wherein $X_4$ represents an amino acid residue I or L;
wherein $X_5$ represents an amino acid residue S or A;
wherein $X_6$ represents an amino acid residue A, E or N; preferably, A or N;
wherein $X_7$ represents an amino acid residue N or H;
wherein $X_8$ represents an amino acid residue L or I; and
wherein $X_9$ represents an amino acid residue I or V.

Preferably, such a C-terminal capping module comprising the sequence motif of SEQ ID NO:6, 7 or 8 has an amino acid residue A, I or K; preferably, I or K; at the position corresponding to position 3 of said sequence motif.

Also preferably, such a C-terminal capping module comprising the sequence motif of SEQ ID NO:6, 7 or 8 has an amino acid residue R or D at the position corresponding to position 14 of said sequence motif.

A preferred C-terminal capping module is a C-terminal capping module having the amino acid sequence QDKSGKTPADLAADAGHEDIAEVLQKAA (SEQ ID NO:9).

Further preferred is a C-terminal capping module having the amino acid sequence of SEQ ID NO:9, wherein
the amino acid residue at position 1 is Q or K;
the amino acid residue at position 4 is S or F;
the amino acid residue at position 9 is A or F;
the amino acid residue at position 13 is A or I;
the amino acid residue at position 15 is A, E or N; and
wherein said C-terminal capping module has not the amino acid sequence of SEQ ID NO:2, 3 or 4.

Further preferred is a C-terminal capping module having an amino acid sequence comprising at least 70%, preferably at least 75%, 80%, 85%, 90%, or most preferred at least 95% amino acid sequence identity on alignment with SEQ ID NO:9 or 2. Preferably, the amino acid residue of said C-terminal capping module at the position corresponding to position 4 of SEQ ID NO:9 on alignment is S, the amino acid residue of said C-terminal capping module at the position corresponding to position 9 of SEQ ID NO:9 on alignment is A, the amino acid residue of said C-terminal capping module at the position corresponding to position 13 of SEQ ID NO:9 on alignment is A, and/or the amino acid residue of said C-terminal capping module at the position corresponding to position 15 of SEQ ID NO:9 on alignment is A. Further preferably, the amino acid residue of said C-terminal capping module at the position corresponding to position 9 of SEQ ID NO:9 on alignment is A and/or the amino acid residue of said C-terminal capping module at the position corresponding to position 13 of SEQ ID NO:9 on alignment is A. Also preferably, said C-terminal capping module comprises 28 amino acids.

Further preferred is a C-terminal capping module having the amino acid sequence of SEQ ID NO:2 or 9, wherein
one or more of the amino acid residues of said C-terminal capping module are exchanged by an amino acid found at the corresponding position on alignment of a corresponding C-terminal capping repeat or capping unit and wherein the amino acid residue at position 4 is S;

the amino acid residue at position 9 is A;
the amino acid residue at position 13 is A; and/or
the amino acid residue at position 15 is A.

Preferably, up to 30% of the amino acid residues of said C-terminal capping module are exchanged, more preferably, up to 20% and even more preferably, up to 10% of the amino acid residues are exchanged. Also preferably, such a C-terminal capping module is a naturally occurring C-terminal capping repeat.

Also preferred is a C-terminal capping module comprising the amino acids from position 1 to 25 or from position 1 to 26 of any of the above C-terminal capping modules based on SEQ ID NO:9.

Further preferred is such a C-terminal capping module having an amino acid sequence not comprising the amino acid N followed by G.

Also preferred is a C-terminal capping module having an at least 70%, preferably at least 75%, 80%, 85%, 90%, or most preferred at least 95% amino acid sequence identity with any of the above C-terminal capping modules based on SEQ ID NO:9 or with SEQ ID NO:9 itself.

Further preferred is a C-terminal capping module having an at least 70%, preferably at least 75%, 80%, 85%, 90%, or most preferred at least 95% amino acid sequence identity with SEQ ID NO:2 or 9 and wherein said C-terminal capping module has amino acid A at position 9; preferably, said C-terminal capping module has amino acid A at positions 9 and 13; more preferably, said C-terminal capping module has amino acid A at positions 9, 13 and 15; and most preferably, said C-terminal capping module has amino acid A at positions 9, 13 and 15 and S at position 4.

Further preferred is such a C-terminal capping module not having the amino acid R at position 14 and/or not having the amino acid E at position 15.

Also preferred is such an C-terminal capping module not having an amino acid sequence identical to SEQ ID NO:2, 3 or 4.

Further preferred is such a C-terminal capping module having an amino acid sequence based on SEQ ID NO:9, wherein said C-terminal capping module has amino acids at positions 26, 27 and 28 selected from the group consisting of A, L, R, M, K and N; more preferably, A, L, R and K; and most preferably, K, A and L.

A capping module of a repeat domain can be exchanged by a capping module of the invention by combining techniques, such as alignment of amino acid sequences, mutagenesis and gene synthesis, known to the person skilled in the art. For example, the C-terminal capping repeat of SEQ ID NO:17 can be replaced by C-terminal capping repeat of SEQ ID NO:9 by (i) determination of the C-terminal capping repeat of SEQ ID NO:17 (i.e. sequence position 99 to 126) by sequence alignment with SEQ ID NO:9, (ii) replacing the sequence of the determined C-terminal capping repeat of SEQ ID NO:17 with the sequence of SEQ ID NO:9, (iii) generation of a gene encoding the repeat domain encoding the exchanged C-terminal capping module, (iv) expressing of the modified repeat domain in the cytoplasm of E. coli and (v) purification of the modified repeat domain by standard means.

Furthermore, a repeat domain of the invention can be constructed genetically by assembling a N-terminal capping module (i.e. the N-terminal capping repeat of SEQ ID NO:1) followed by one or more repeat modules (i.e. the repeat modules comprising the amino acid residues from position 33 to 98 of SEQ ID NO:17) and a C-terminal capping module (i.e. the C-terminal capping repeat of SEQ ID NO:9) by means of gene synthesis. The genetically assembled repeat domain gene can then be expressed in E. coli as described above.

Also preferred is a binding protein, wherein the ankyrin repeat domain or designed ankyrin repeat domain comprises a C-terminal capping module with the sequence motif of SEQ ID NO:6, 7 or 8, wherein said capping module has the amino acid I at position 3 and wherein said repeat module is preceded by a repeat module with the ankyrin repeat sequence motif of SEQ ID NO:12.

Further preferred is a binding protein, a repeat domain, an N-terminal capping module or a C-terminal capping module having an amino acid sequence devoid of amino acids C, M or N.

Further preferred is a binding protein, a repeat domain, an N-terminal capping module or a C-terminal capping module having an amino acid sequence devoid of amino acid N followed by G.

Further preferred is any such C-terminal capping module comprising a C-terminal capping repeat, wherein one or more of the amino acids residues in said capping repeat are replaced by an amino acid residue found at the corresponding position on alignment of a corresponding capping unit or repeat unit.

Further preferred is a binding protein comprising any such N-terminal or C-terminal capping module.

Examples of amino acid sequences of such C-terminal capping modules are the amino acid sequences from position 99 to 126 in SEQ ID NOs:19, 21, 27, 28, 38, 40 and 42. Example 6 demonstrates that the thermal stability of a repeat domain can be increased by replacing their C-terminal capping modules by a capping module of the invention.

The term "target" refers to an individual molecule such as a nucleic acid molecule, a polypeptide or protein, a carbohydrate, or any other naturally occurring molecule, including any part of such individual molecule, or complexes of two or more of such molecules. The target may be a whole cell or a tissue sample, or it may be any non-natural molecule or moiety. Preferably, the target is a naturally occurring or non-natural polypeptide or a polypeptide containing chemical modifications, for example modified by natural or non-natural phosphorylation, acetylation, or methylation. In the particular application of the present invention, the target is xSA.

The term "xSA" refers to a mammalian serum albumin, such as a serum albumin from mouse, rat, rabbit, dog, pig, monkey or human. The term "MSA" refers to a mouse serum albumin (UniProtKB/Swiss-Prot primary accession number P07724), the term "CSA" refers to a cynomolgus monkey (i.e. macaca fascicularis) serum albumin (UniProtKB/Swiss-Prot primary accession number A2V9Z4) and the term "HSA" refers to a human serum albumin (UniProtKB/Swiss-Prot primary accession number P02768).

The term "consensus sequence" refers to an amino acid sequence, wherein said consensus sequence is obtained by structural and/or sequence aligning of multiple repeat units. Using two or more structural and/or sequence aligned repeat units, and allowing for gaps in the alignment, it is possible to determine the most frequent amino acid residue at each position. The consensus sequence is that sequence which comprises the amino acids which are most frequently represented at each position. In the event that two or more amino acids are represented above-average at a single position, the consensus sequence may include a subset of those amino acids. Said two or more repeat units may be taken from the repeat units comprised in a single repeat protein, or from two or more different repeat proteins.

Consensus sequences and methods to determine them are well known to the person skilled in the art.

A "consensus amino acid residue" is the amino acid found at a certain position in a consensus sequence. If two or more, e.g. three, four or five, amino acid residues are found with a similar probability in said two or more repeat units, the consensus amino acid may be one of the most frequently found amino acids or a combination of said two or more amino acid residues.

Further preferred are non-naturally occurring capping modules, repeat modules, binding proteins or binding domains.

The term "non-naturally occurring" means synthetic or not from nature, more specifically, the term means made from the hand of man. The term "non-naturally occurring binding protein" or "non-naturally occurring binding domain" means that said binding protein or said binding domain is synthetic (i.e. produced by chemical synthesis from amino acids) or recombinant and not from nature. "Non-naturally occurring binding protein" or "non-naturally occurring binding domain" is a man-made protein or domain, respectively, obtained by expression of correspondingly designed nucleic acids. Preferably, the expression is done in eukaryotic or bacterial cells, or by using a cell-free in vitro expression system. Further, the term means that the sequence of said binding protein or said binding domain is not present as a non-artificial sequence entry in a sequence database, for example in GenBank, EMBL-Bank or Swiss-Prot. These databases and other similar sequence databases are well known to the person skilled in the art.

The invention relates to a binding protein comprising a binding domain, wherein said binding domain is an ankyrin repeat domain and specifically binds to xSA and wherein said binding protein and/or binding domain has a midpoint denaturation temperature (Tm) above 40° C. upon thermal unfolding in PBS and forms less than 5% (w/w) insoluble aggregates at concentrations up to 10 g/L when incubated at 37° C. for 1 day in PBS.

The term "PBS" means a phosphate buffered water solution containing 137 mM NaCl, 10 mM phosphate and 2.7 mM KCl and having a pH of 7.4.

Preferably, the binding protein and/or binding domain has a midpoint denaturation temperature (Tm) above 45° C., more preferably above 50° C., more preferably above 55° C., and most preferably above 60° C. upon thermal unfolding in PBS at pH 7.4 or in MES buffer at pH 5.8. A binding protein or a binding domain of the invention possesses a defined secondary and tertiary structure under physiological conditions. Thermal unfolding of such a polypeptide results in a loss of its tertiary and secondary structure, which can be followed, for example, by circular dichroism (CD) measurements. The midpoint denaturation temperature of a binding protein or binding domain upon thermal unfolding corresponds to the temperature at the midpoint of the cooperative transition in physiological buffer upon heat denaturation of said protein or domain by slowly increasing the temperature from 10° C. to about 100° C. The determination of a midpoint denaturation temperature upon thermal unfolding is well known to the person skilled in the art. This midpoint denaturation temperature of a binding protein or binding domain upon thermal unfolding is indicative of the thermal stability of said polypeptide.

Also preferred is a binding protein and/or binding domain forming less than 5% (w/w) insoluble aggregates at concentrations up to 20 g/L, preferably up 40 g/L, more preferably up to 60 g/L, even more preferably up to 80 g/L, and most preferably up to 100 g/L when incubated for over 5 days, preferably over 10 days, more preferably over 20 days, more preferably over 40 days, and most preferably over 100 days at 37° C. in PBS. The formation of insoluble aggregates can be detected by the appearance of visual precipitations, gel filtration or dynamic light scattering, which strongly increases upon formation of insoluble aggregates. Insoluble aggregates can be removed from a protein sample by centrifugation at 10,000×g for 10 minutes. Preferably, a binding protein and/or binding domain forms less than 2%, more preferably less than 1%, 0.5%, 0.2%, 0.1%, or most preferably less than 0.05% (w/w) insoluble aggregates under the mentioned incubation conditions at 37° C. in PBS. Percentages of insoluble aggregates can be determined by separation of the insoluble aggregates from soluble protein, followed by determination of the protein amounts in the soluble and insoluble fraction by standard quantification methods.

Also preferred is a binding protein and/or binding domain that does not lose its native three-dimensional structure upon incubation in PBS containing 100 mM dithiothreitol (DTT) for 1 or 10 hours at 37° C.

In one particular embodiment the invention relates to a binding protein comprising a binding domain being an ankyrin repeat domain, specifically binding to xSA and having the indicated or preferred midpoint denaturation temperature and non-aggregating properties as defined above, wherein said binding protein has an at least 5-fold higher terminal plasma half-life in a mammal compared to a binding domain not binding to a serum protein such as xSA.

Preferably, said binding domain has an at least 10-fold, more preferably at least 20-fold, 40-fold, 100-fold, 300-fold, or most preferably at least $10^3$-fold higher terminal plasma half-life in a mammal compared to a binding domain not binding to a serum protein such as xSA.

Also preferably, said binding domain does not bind xSA indicated by a Kd above $10^{-4}$M, more preferably above $10^{-3}$M or most preferably above $10^{-2}$M for binding of xSA. An example of a binding domain that does not bind xSA is the repeat domain of SEQ ID NO:32.

Further preferably, said binding domain is a repeat domain and has an at least 5-fold, more preferably at least 10-fold, 20-fold, 40-fold, 100-fold, 300-fold, or most preferably at least $10^3$-fold higher (i.e. longer) terminal plasma half-life in a mammal compared to the repeat domain of SEQ ID NO:32 or compared to DARPin #32, DARPin #41 or DARPin #42.

A preferred binding protein comprises a binding domain with binding specificity for HSA having a terminal plasma half-life of above 1, more preferably above 3, 5, 7, 10, 15, or most preferably above 20 days in humans.

The terminal plasma half-life of a binding domain can be determined by assays well know to the person skilled in the art (Toutain, P. L., and Bousquet-Mélou, A., J. Vet. Pharmacol. Ther. 27(5), 427-439, 2004). Examples on the determination of terminal plasma half-life are given in the Examples.

The term "terminal plasma half-life" of a drug such as a binding protein or binding domain of the invention refers to the time required to reach half the plasma concentration of the drug applied to a mammal after reaching pseudo-equilibrium. This half-life is not defined as the time required to eliminate half the dose of the drug administered to the mammal.

In one particular embodiment the invention relates to a binding protein comprising a binding domain being an ankyrin repeat domain, specifically binding to xSA and comprising a bioactive compound.

The term "bioactive compound" refers to a compound that is disease modifying when applied to a mammal having said disease. A bioactive compound may have antagonistic or agonistic properties and can be a proteinaceous bioactive compound or a non-proteinaceous bioactive compound.

Such proteinaceous bioactive compounds can be covalently attached to, for example, a binding domain of the invention by the generation of genetic fusion polypeptides using standard DNA cloning technologies, followed by their standard expression and purification. For example, DARPin #36 comprises a repeat domain with binding specificity for a human growth factor (i.e. a bioactive compound) followed by a repeat domain with binding specificity for HSA.

Such non-proteinaceous bioactive compounds can be covalently attached to, for example, a binding domain of the invention by chemical means, e.g., by coupling to a cysteine thiol via a maleimide linker with a cysteine being coupled via a peptide linker to the N- or C-terminus of a binding domain as described herein.

Examples of proteinaceous bioactive compounds are binding domains having a distinct target specificity (e.g. neutralizing a growth factor by binding to it), cytokines (e.g. interleukins), growth factors (e.g. human growth hormone), antibodies and fragments thereof, hormones (e.g. GLP-1) and any possible proteinaceous drug.

Examples of non-proteinaceous bioactive compounds are, toxins (e.g. DM1 from ImmunoGen), small molecules targeting GPCRs, antibiotics and any possible non-proteinaceous drug.

In one particular embodiment the invention relates to a binding protein comprising an ankyrin repeat domain specifically binding to xSA and further comprising a bioactive compound, wherein said binding protein has an at least 2-fold higher terminal half-life in a mammal compared to the terminal half-life of said unmodified bioactive compound, wherein said higher terminal half-life is conferred to said binding protein by said repeat domain.

Preferably, said binding protein has an at least 5-fold, more preferably at least 10-fold, 20-fold, 40-fold, 100-fold, 300-fold, or most preferably at least $10^3$-fold higher terminal plasma half-life in a mammal compared to said unmodified bioactive compound.

Another preferred embodiment is a recombinant binding protein comprising a binding domain specifically binding to xSA and wherein said binding domain is an ankyrin repeat domain or a designed ankyrin repeat domain. Such an ankyrin repeat domain may comprise one, two, three or more internal repeat modules that will participate in binding to xSA. Preferably, such an ankyrin repeat domain comprises an N-terminal capping module, two to four internal repeat modules, and a C-terminal capping module. Preferably, said binding domain is an ankyrin repeat domain or designed ankyrin repeat domain. Also preferably, said capping modules are capping repeats.

In particular, the invention relates to a binding protein as defined herein above, wherein the ankyrin repeat domain competes for binding to a mammalian serum albumin with an ankyrin repeat domain selected from the group consisting of SEQ ID NOs: 17 to 31 and 43 to 48; preferably SEQ ID NOs: 17 to 31; more preferably SEQ ID NO:19, 21, 27 and 28, in particular SEQ ID NO:19 and 27.

Most preferred is a binding protein, wherein the ankyrin repeat domain is selected from the group consisting of SEQ ID NOs: 17 to 31 and 43 to 48, wherein G at position 1 and/or S at position 2 of said ankyrin repeat domain are optionally missing.

Also preferably said repeat domain competes for binding to xSA with a binding protein selected from the group of DARPins #17 to 31 and 43 to 48. Preferably, said repeat domain competes for binding to xSA with a binding protein from the group of DARPins #19, 21, 27, 28, 45, 46, 47 and 48. More preferably, said repeat domain competes for binding to xSA with binding protein DARPin #19, 45, 46, 48 or 27; even more preferably, said repeat domain competes for binding to xSA with the binding protein DARPin #46 or 27.

The term "compete for binding" means the inability of two different binding domains of the invention to bind simultaneously to the same target, while both are able to bind the same target individually. Thus, such two binding domains compete for binding to said target. Preferably, said two competing binding domains bind to an overlapping or the same binding epitope on said target. Methods, such as competition Enzyme-Linked Immuno Sorbent Assay (ELISA) or competition SPR measurements (e.g. by using the Proteon instrument from BioRad), to determine if two binding domains compete for binding to a target, are well known to the practitioner in the art.

Another preferred embodiment is a binding protein comprising a repeat domain with binding specificity for xSA selected from the group consisting of the repeat domains of SEQ ID NO:17 to 31. Preferably, said repeat domain is the repeat domain of SEQ ID NO:19, 21, 27 or 28. More preferably, said repeat domain is the repeat domain of SEQ ID NO:19. Also more preferably, said repeat domain is the repeat domain of SEQ ID NO:21. Also more preferably, said repeat domain is the repeat domain of SEQ ID NO:27. Also more preferably, said repeat domain is the repeat domain of SEQ ID NO:28.

Further preferred is a binding protein, wherein said repeat domain with binding specificity for xSA comprises an amino acid sequence that has at least 70% amino acid sequence identity with a repeat domain of said group of repeat domains. Preferably, said amino acid sequence identity is at least 75%, more preferably at least 80%, more preferably at least 85%, more preferably at least 90%, and most preferably at least 95%.

Further preferred is a binding protein, wherein said repeat domain with binding specificity for xSA comprises a repeat module that has at least 70% amino acid sequence identity with a repeat module of a repeat domain of said group of repeat domains. Preferably, said amino acid sequence identity is at least 75%, more preferably at least 80%, more preferably at least 85%, more preferably at least 90%, and most preferably at least 95%.

Further preferred is a binding protein, wherein said binding protein comprises two or more of said repeat domains with binding specificity for xSA. Preferably, said binding protein comprises 2 or 3 of said repeat domains. Said two or more repeat domains have the same or different amino acid sequence.

In a further preferred embodiment of a binding protein comprising a repeat domain according to the present invention, one or more of the amino acid residues of the repeat modules of said repeat domain are exchanged by an amino acid residue found at the corresponding position on alignment of a repeat unit. Preferably, up to 30% of the amino acid residues are exchanged, more preferably, up to 20%, and even more preferably, up to 10% of the amino acid residues are exchanged. Most preferably, such a repeat unit is a naturally occurring repeat unit.

In a further preferred embodiment of a binding protein comprising a repeat domain according to the present invention, one or more of the amino acid residues of the N-terminal capping module of said repeat domain is exchanged by an amino acid residue found at the corresponding position on alignment of an N-terminal capping unit. Preferably, up to 30% of the amino acid residues are exchanged, more preferably, up to 20%, and even more preferably, up to 10% of the amino acid residues are exchanged. Most preferably, such an N-terminal capping unit is a naturally occurring N-terminal capping unit.

In a further preferred embodiment of a binding protein comprising a repeat domain according to the present invention, one or more of the amino acid residues of the C-terminal capping module of said repeat domain is exchanged by an amino acid residue found at the corresponding position on alignment of a C-terminal capping unit. Preferably, up to 30% of the amino acid residues are exchanged, more preferably, up to 20%, and even more preferably, up to 10% of the amino acid residues are exchanged. Most preferably, such a C-terminal capping unit is a naturally occurring C-terminal capping unit.

In still another particular embodiment, up to 30% of the amino acid residues, more preferably, up to 20%, and even more preferably, up to 10% of the amino acid residues are exchanged with amino acids which are not found in the corresponding positions of repeat units, N-terminal capping units or C-terminal capping units.

In further embodiments, any of the xSA binding proteins or domains described herein may be covalently bound to one or more additional moieties, including, for example, a moiety that binds to a different target to create a dual-specificity binding agent, a bioactive compound, a labeling moiety (e.g. a fluorescent label such as fluorescein, or a radioactive tracer), a moiety that facilitates protein purification (e.g. a small peptide tag, such as a His- or strep-tag), a moiety that provides effector functions for improved therapeutic efficacy (e.g. the Fc part of an antibody to provide antibody-dependent cell-mediated cytotoxicity, a toxic protein moiety such as Pseudomonas aeruginosa exotoxin A (ETA) or a small molecular toxic agent such as maytansinoids or DNA alkylating agents) or a moiety that provides improved pharmacokinetics. Improved pharmacokinetics may be assessed according to the perceived therapeutic need. Often it is desirable to increase bioavailability and/or increase the time between doses, possibly by increasing the time that a protein remains available in the serum after dosing. In some instances, it is desirable to improve the continuity of the serum concentration of the protein over time (e.g., decrease the difference in serum concentration of the protein between the concentration shortly after administration and the concentration shortly before the next administration).

In a further embodiment, the invention relates to nucleic acid molecules encoding the particular binding proteins, the particular N-terminal capping modules or the particular C-terminal capping modules. Further, a vector comprising said nucleic acid molecule is considered.

Further, a pharmaceutical composition comprising one or more of the above mentioned binding proteins, in particular binding proteins comprising repeat domains, or nucleic acid molecules encoding the particular binding proteins, and optionally a pharmaceutical acceptable carrier and/or diluent is considered. Pharmaceutical acceptable carriers and/or diluents are known to the person skilled in the art and are explained in more detail below. Even further, a diagnostic composition comprising one or more of the above mentioned binding proteins, in particular binding proteins comprising repeat domains, is considered.

A pharmaceutical composition comprises binding proteins as described above and a pharmaceutically acceptable carrier, excipient or stabilizer, for example as described in Remington's Pharmaceutical Sciences 16$^{th}$ edition, Osol, A. Ed. [1980]. Suitable carriers, excipients or stabilizers known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. A pharmaceutical composition may also be a combination formulation, comprising an additional active agent, such as an anti-cancer agent or an anti-angiogenic agent.

The formulations to be used for in vivo administration must be aseptic or sterile. This is readily accomplished by filtration through sterile filtration membranes.

The pharmaceutical composition may be administered by any suitable method within the knowledge of the skilled man. The preferred route of administration is parenterally. In parenteral administration, the medicament of this invention will be formulated in a unit dosage injectable form such as a solution, suspension or emulsion, in association with a pharmaceutically acceptable excipients as defined above. The dosage and mode of administration will depend on the individual to be treated and the particular disease. Generally, the pharmaceutical composition is administered so that the binding protein of the present invention is given at a dose between 1 µg/kg and 20 mg/kg, more preferably between 10 µg/kg and 5 mg/kg, most preferably between 0.1 and 2 mg/kg. Preferably, it is given as a bolus dose. Continuous infusion may also be used and includes continuous subcutaneous delivery via an osmotic minipump. If so, the pharmaceutical composition may be infused at a dose between 5 and 20 µg/kg/minute, more preferably between 7 and 15 µg/kg/minute.

Further, any of the above mentioned pharmaceutical composition is considered for the treatment of a disorder.

The invention further provides methods of treatment. The method comprises administering, to a patient in need thereof, a therapeutically effective amount of a binding protein of the invention.

Further, a method of treating a pathological condition in a mammal including man, comprising administering to a patient in need thereof an effective amount of the above mentioned pharmaceutical composition is considered.

The binding protein according to the invention may be obtained and/or further evolved by several methods such as display on the surface of bacteriophages (WO 1990/002809, WO 2007/006665) or bacterial cells (WO 1993/010214), ribosomal display (WO 1998/048008), display on plasmids (WO 1993/008278) or by using covalent RNA-repeat protein hybrid constructs (WO 2000/032823), or intracellular expression and selection/screening such as by protein complementation assay (WO 1998/341120). Such methods are known to the person skilled in the art.

A library of ankyrin repeat proteins used for the selection/screening of a binding protein according to the invention may be obtained according to protocols known to the person skilled in the art (WO 2002/020565, Binz, H. K., et al., J. Mol. Biol., 332, 489-503, 2003, and Binz et al., 2004, loc. cit.). The use of such a library for the selection xSA specific DARPins is given in Example 1. In analogy, the ankyrin repeat sequence motifs as presented above can be used to build libraries of ankyrin repeat proteins that may be used for the selection or screening of xSA specific DARPins.

Furthermore, repeat domains of the present invention may be modularly assembled from repeat modules according to the current invention and appropriate capping modules or capping repeats (Forrer, P., et al., FEBS letters 539, 2-6, 2003) using standard recombinant DNA technologies (e.g. WO 2002/020565, Binz et al., 2003, loc. cit. and Binz et al., 2004, loc. cit).

The invention is not restricted to the particular embodiments described in the Examples. Other sources may be used and processed following the general outline described below.

EXAMPLES

All of the starting materials and reagents disclosed below are known to those skilled in the art, and are available commercially or can be prepared using well-known techniques.

Materials

Chemicals were purchased from Fluka (Switzerland). Oligonucleotides were from Microsynth (Switzerland). Unless stated otherwise, DNA polymerases, restriction enzymes and buffers were from New England Biolabs (USA) or Fermentas (Lithuania). The cloning and protein production strain was E. coli XL1-blue (Stratagene, USA) or BL21 (Novagen, USA). Purified serum albumin and sera from different species were purchased (e.g. from Sigma-Aldrich, Switzerland or Innovative Research, USA). Biotinylated serum albumin of different species was obtained chemically via coupling of the biotin moiety to primary amines of the purified serum albumins using standard biotinylation reagents and methods (Pierce, USA).

Molecular Biology

Unless stated otherwise, methods are performed according to described protocols (Sambrook J., Fritsch E. F. and Maniatis T., Molecular Cloning: A Laboratory Manual, Cold Spring Harbor Laboratory 1989, New York).

Designed Ankyrin Repeat Protein Libraries

The N2C and N3C designed ankyrin repeat protein libraries are described (WO 2002/020565; Binz et al. 2003, loc. cit.; Binz et al. 2004, loc. cit.). The digit in N2C and N3C describes the number of randomized repeat modules present between the N-terminal and C-terminal capping modules. The nomenclature used to define the positions inside the repeat units and modules is based on Binz et al. 2004, loc. cit. with the modification that borders of the ankyrin repeat modules and ankyrin repeat units are shifted by one amino acid position. For example, position 1 of an ankyrin repeat module of Binz et al. 2004 (loc. cit.) corresponds to position 2 of a ankyrin repeat module of the current disclosure and consequently position 33 of a ankyrin repeat module of Binz et al. 2004. loc. cit. corresponds to position 1 of a following ankyrin repeat module of the current disclosure.

All the DNA sequences were confirmed by sequencing, and the calculated molecular weight of all described proteins was confirmed by mass spectrometry.

Example 1

Selection of Binding Proteins Comprising a Repeat Domain with Binding Specificity for xSA Using ribosome display (Hanes, J. and Plückthun, A., PNAS 94, 4937-42, 1997) many designed ankyrin repeat proteins (DARPins) with binding specificity for xSA were selected from the N2C or N3C DARPin libraries described by Binz et al. 2004 (loc. cit.). The binding of the selected clones toward specific (xSA; i.e. MSA, HSA or CSA) and unspecific (MBP, E. coli maltose binding protein) targets was assessed by crude extract ELISA indicating that xSA binding proteins were successfully selected. The repeat domains of SEQ ID NO:17 to 31 constitute amino acid sequences of selected binding proteins comprising a repeat domain with binding specificity for xSA. Sequence analysis of selected binders revealed specific ankyrin repeat sequence motifs inherent to certain selected families of binders. Such ankyrin repeat sequence motifs present in repeat domains with binding specificity for xSA are provided in SEQ ID NO:11 to 14.

Selection of Serum Albumin Specific Ankyrin Repeat Proteins by Ribosome Display

The selection of serum albumin specific ankyrin repeat proteins was performed by ribosome display (Hanes and Plückthun, loc. cit.) using HSA, CSA or MSA as target proteins, the library of designed ankyrin repeat proteins as described (WO 2002/020565, Binz et al., 2003, loc. cit. and Binz et al., 2004, loc. cit) and established protocols (Zahnd, C., Amstutz, P. and Plückthun, A., Nat. Methods 4, 69-79, 2007). Ribosome-display selection rounds were performed on HSA, CSA or MSA (including biotinylated variants of HSA or MSA immobilized over neutravidin or streptavidin) with both the N2C and N3C DARPin libraries using established protocols (Binz et al. 2004, loc. cit.). The number of reverse transcription (RT)-PCR cycles after each selection round was constantly reduced from 40 to 30, adjusting to the yield due to enrichment of binders. Four selection rounds on HSA, CSA or MSA yielded pools of micromolar to nanomolar-affinity DARPins, as revealed by ELISA and SPR measurements of single clones. The affinity of certain DARPins was further improved by using affinity maturation by methods well known to the person skilled in the art (e.g. by diversifying of DARPin clones by error prone PCR and selection and screening for improved binders as described above).

Selected Clones Bind Specifically to Serum Albumin as Shown by Crude Extract ELISA Individual selected DARPins specifically binding xSA were identified by an enzyme-linked immunosorbent assay (ELISA) using crude Escherichia coli extracts of DARPin expression cells using standard protocols. By ribosome display selected clones were cloned into the pQE30 (Qiagen) expression vector, transformed into E. coli XL1-Blue (Stratagene) and then grown overnight at 37° C. in a 96-deep-well plate (each clone in a single well) containing 1 ml growth medium (2YT containing 1% glucose and 100 µg/ml ampicillin). 1 ml of fresh 2YT containing 50 µg/ml ampicillin was inoculated with 100 µl of the overnight culture in a fresh 96-deep-well plate. After incubation for 2 h at 37° C., expression was induced with IPTG (1 mM final concentration) and continued for 3 h. Cells were harvested, resuspended in 100 µl B-PERII (Pierce) and incubated for 15 min at room temperature with shaking. Then, 900 µl PBS-TC (PBS supplemented with 0.25% Casein hydrolysate, 0.1% Tween 20®, pH 7.4) were added and cell debris were removed by centrifugation. 100 µl of each lysed clone were applied to a well of a NeutrAvidin coated MaxiSorp plate containing either xSA or the unrelated MBP immobilized via their biotin moiety and incubated for 1 h at RT. After extensive washing with PBS-T (PBS supplemented with 0.1% Tween 20®, pH 7.4) the plate was developed using standard ELISA procedures using the monoclonal anti-RGS (His)$_4$ antibody (34650, Qiagen) as primary antibody and a polyclonal goat anti-mouse antibody conjugated with alkaline phosphatase (A3562, Sigma) as secondary reagent.

Binding was then detected by using disodium 4-nitrophenyl phosphate (4NPP, Fluka) as a substrate for alkaline phosphatase. The color development was measured at 405 nm. Screening of several hundred clones by such a crude cell extract ELISA revealed more than hundred different DARPins with specificity for xSA. These binding proteins were chosen for further analysis. Examples of amino acid sequences of selected repeat domains that specifically bind to xSA are provided in SEQ ID NO:17 to 31, 37 to 40, and 43 to 48.

Deducing Repeat Sequence Motives from Selected Repeat Domains with Binding Specificity for xSA The amino acid sequences of selected repeat domains with binding specificity for xSA were further analyzed by sequence analyzing tools known to the practitioner in the art (WO 2002/020565; Forrer et al., 2003, loc. cit.; Forrer, P., Binz, H. K., Stumpp, M. T. and Plückthun, A., ChemBioChem, 5(2), 183-189, 2004). Nevertheless, in contrast to WO 2002/020565 where naturally occurring repeat motifs were used to deduce repeat sequence motifs, here the repeat sequence motifs were deduced from the repeat units of selected repeat domains with binding specificity for xSA. Thereby families of selected repeat domains comprising a common repeat sequence motif were determined. Such repeat sequence motifs present in repeat domains with binding specificity for xSA are provided in SEQ ID NO:11 to 14.

High Level and Soluble Expression of DARPins

For further analysis, the selected clones showing specific xSA binding in the crude cell extract ELISA as described above were expressed in *E. coli* BL21 or XL1-Blue cells and purified using their His-tag using standard protocols. 25 ml of stationary overnight cultures (LB, 1% glucose, 100 mg/l of ampicillin; 37° C.) were used to inoculate 1 l cultures (same medium). At an absorbance of 0.7 at 600 nm, the cultures were induced with 0.5 mM IPTG and incubated at 37° C. for 4 h. The cultures were centrifuged and the resulting pellets were resuspended in 40 ml of TBS500 (50 mM Tris-HCl, 500 mM NaCl, pH 8) and sonicated. The lysate was recentrifuged, and glycerol (10% (v/v) final concentration) and imidazole (20 mM final concentration) were added to the resulting supernatant. Proteins were purified over a Ni-nitrilotriacetic acid column (2.5 ml column volume) according to the manufacturer's instructions (QIAgen, Germany). Alternatively, DARPins or selected repeat domains devoid of a 6×His-tag were purified by anion exchange chromatography followed by size exclusion chromatography according to standard resins and protocols known to the person skilled in the art. Up to 200 mg of highly soluble DARPins with binding specificity to serum albumin can be purified from one liter of *E. coli* culture with a purity >95% as estimated from SDS-15% PAGE. Such purified DARPins are used for further characterizations.

Example 2

Stability Analysis and Size Exclusion Chromatography of DARPins with Binding Specificity for xSA DARPins #19 to 22 and DARPins #27 to 30 with binding specificity for xSA were purified to near homogeneity using their His-tag as described above and stored in PBS for 28 days at 30 mg/ml (~2 mM) at 40° C. (stability study). At day 0 (FIG. 1A) and day 28 (FIG. 1B) samples were taken, diluted to 500 μM and analyzed by size exclusion chromatography (SEC) to assess their apparent molecular weight and stability (i.e. their aggregation, multimerization or degradation tendency) over time.

In a further experiment (FIG. 1C), DARPins #19 and 43 to 48 with binding specificity for xSA were purified to near homogeneity using their His-tag as described above and stored in PBS for 28 days at around 100 mg/ml at −80° C., diluted to 500 μM and analyzed by size exclusion chromatography (SEC) for characterization (i.e. their aggregation, multimerization or degradation tendency). Notably, a larger column was used compared to the first analysis series (see below).

Size Exclusion Chromatography (SEC)

Analytical SEC was carried out using a HPLC system (Agilent 1200 series) using either a Superdex 200 5/150 column (FIG. 1A and FIG. 1B) or Superdex 200 10/300GL column (FIG. 1C) (GE Healthcare) at 20° C. The Superdex 200 5/150 column has a bed volume of 3.0 ml, and a void volume of 1.08 ml (experimentally determined using blue dextran). The Superdex 200 10/300GL column has a bed volume of 24 ml, and a void volume of about 8 ml. The measurements were performed according to standard procedures known to the person skilled in the art. Runs were done at a flow rate of 0.2 ml/min and a maximum pressure of 15 bar (Superdex 200 5/150) or 0.6 ml/min and a maximum pressure of 18 bar (Superdex 200 10/300GL) in PBS. Samples of proteins were diluted in PBS to about 20-500 μM, filtered (0.22 μm), and 20-100 μl of the diluted samples were injected on the column for separation. Elution profiles of protein samples were recorded by reading the absorbance at 280 nm. Aprotinin (AP) with a molecular weight of 6.5 kDa, Carbonic Anhydrase (CA) with a molecular weight of 29 kDa and Conalbumin (CO) with a molecular weight of 75 kDa were used as standard proteins to obtain a calibration curve from which the apparent molecular weights of the sample proteins can be determined.

Figure 1A:
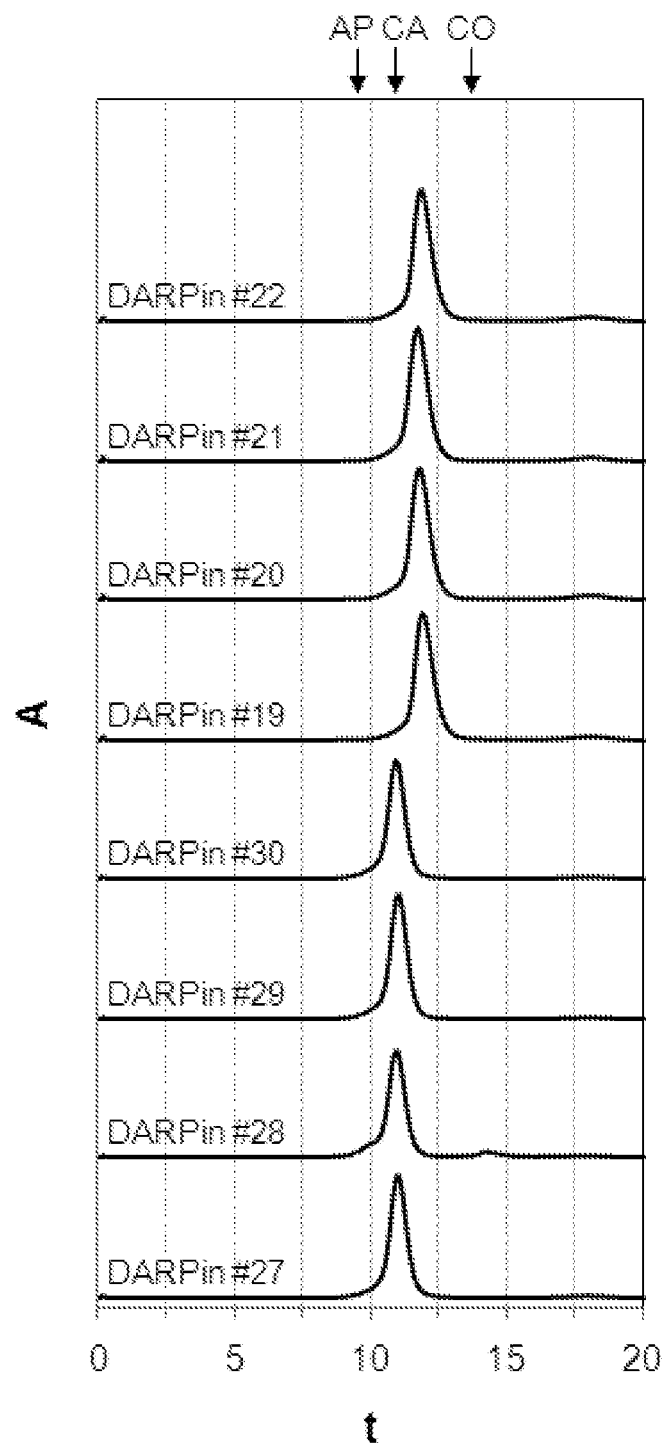
FIGS. 1A to 1C. Stability Analysis of Selected DARPins by SEC.
Figure 1B:
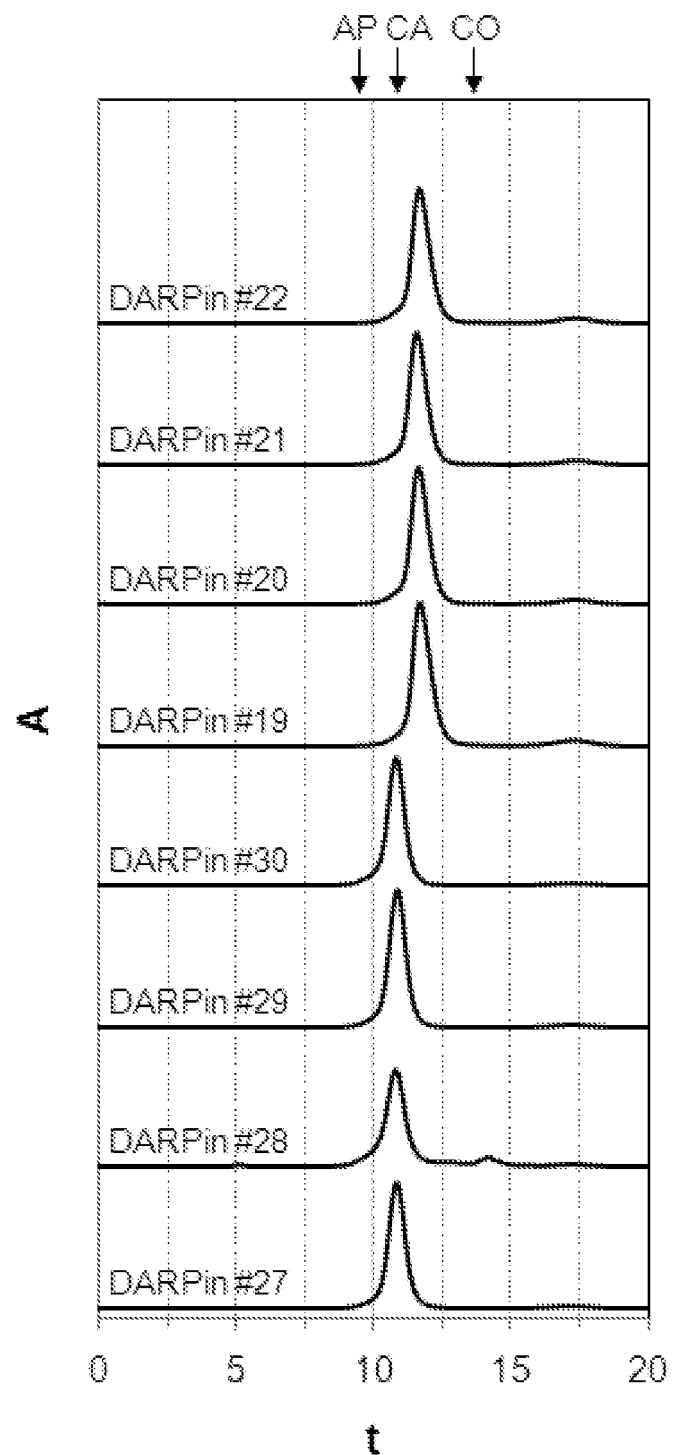
Figure 1C:
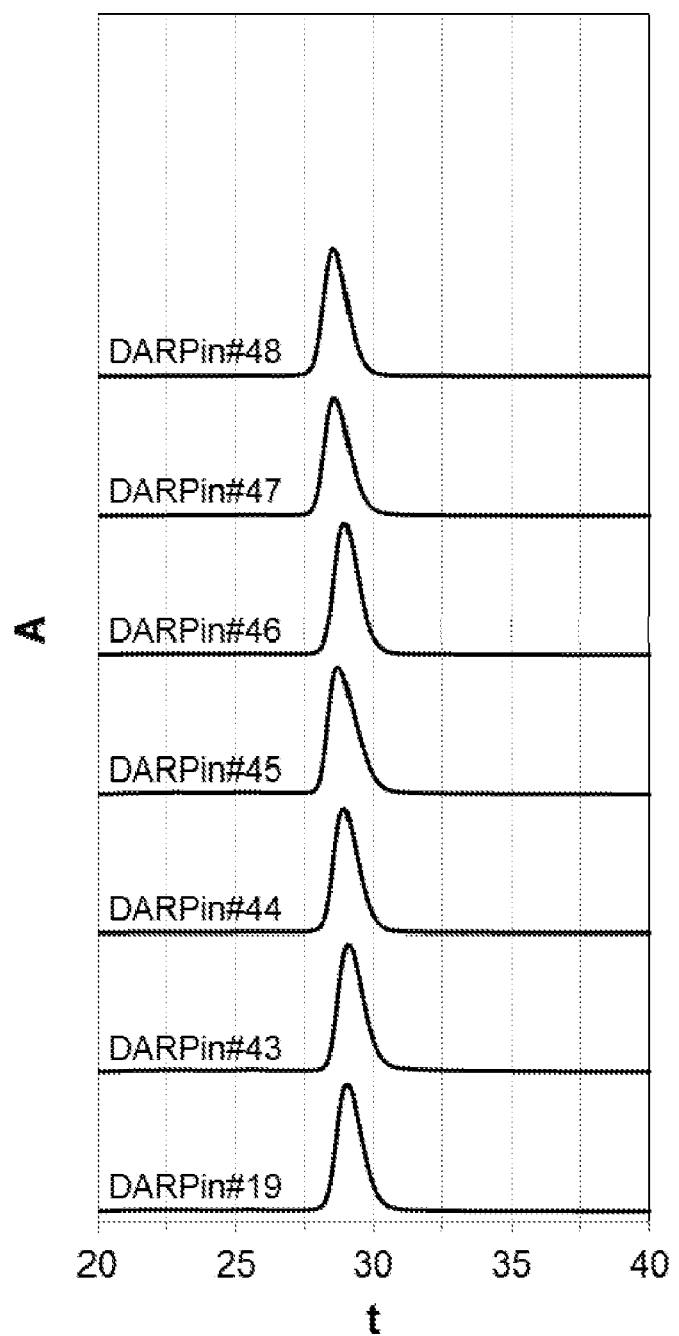
Figure 2A:
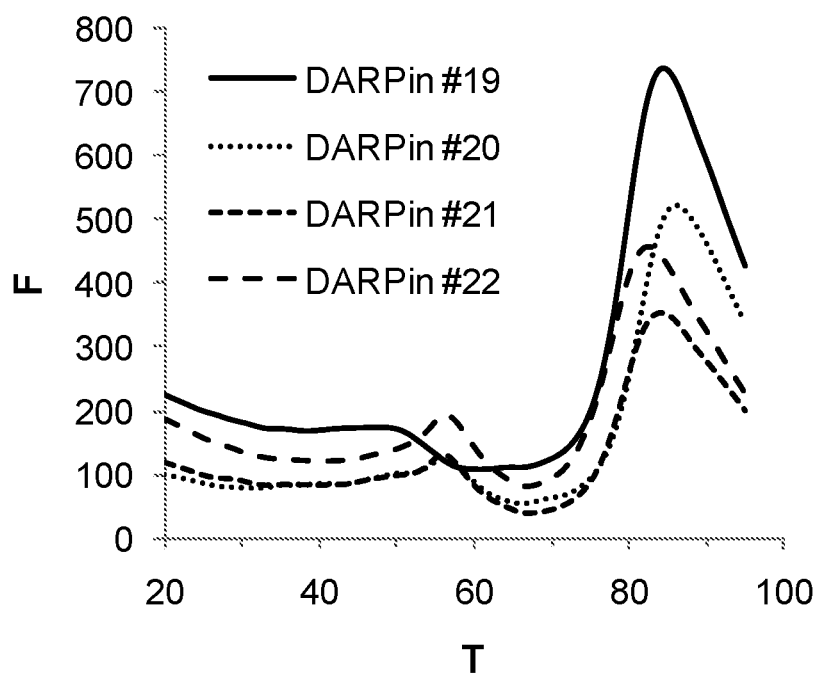
Figure 2B:
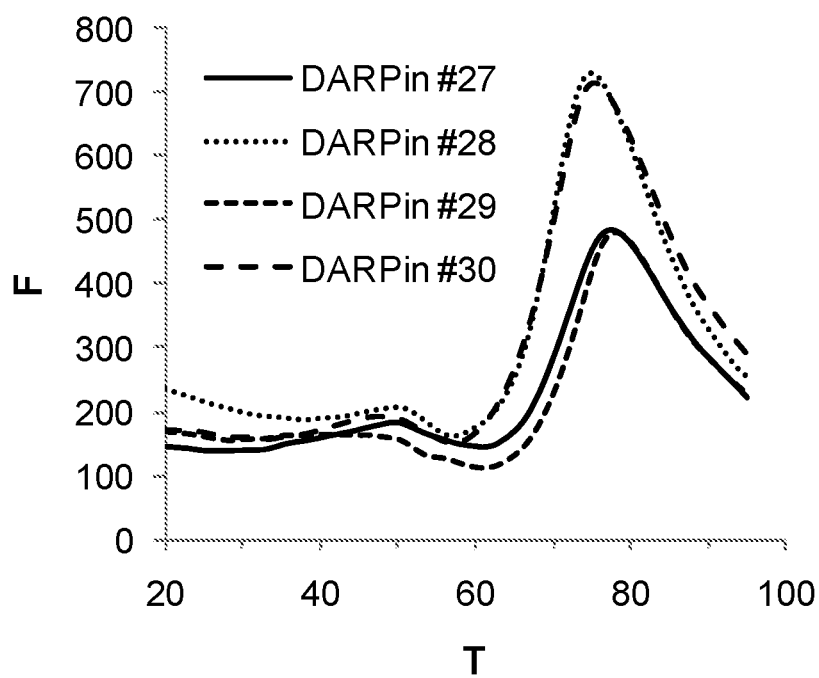
Figure 2C:
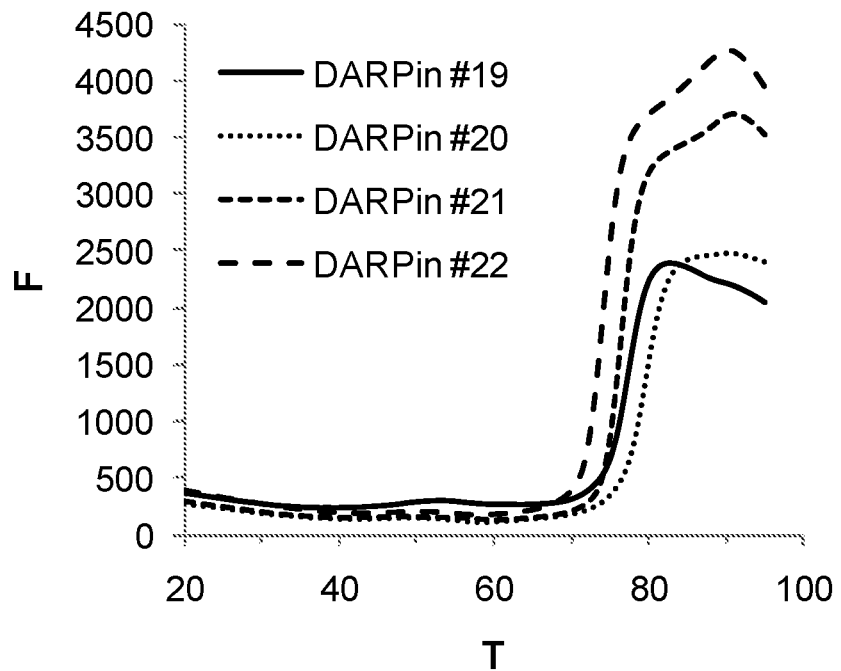
Figure 2D:
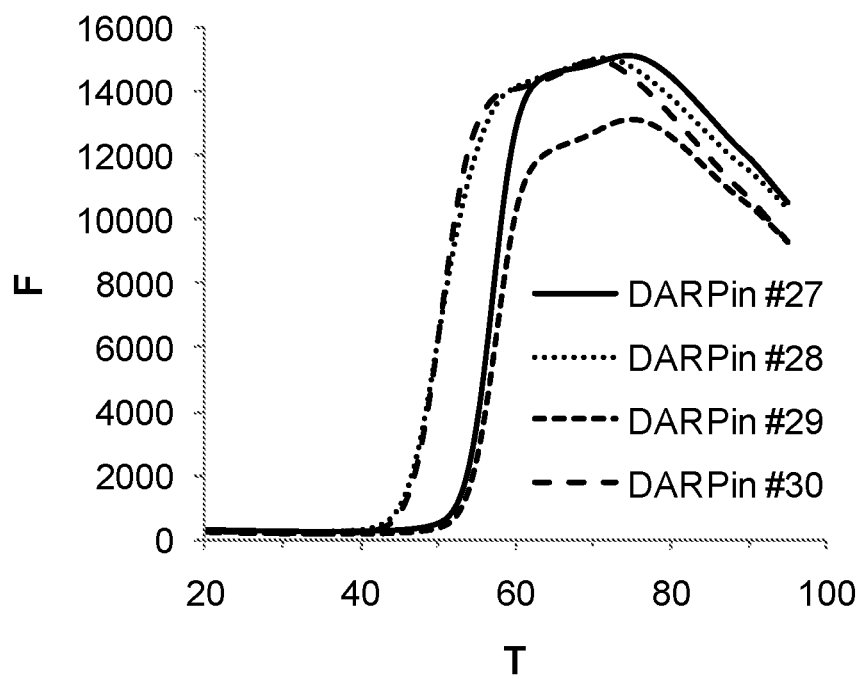

The results are shown in FIGS. 1A to 1C. DARPins #19-22 and 27-30 show indistinguishable SEC chromatograms (i.e. indistinguishable elution profiles) at day 0 and day 28 of the stability study. Conclusively, all DARPins elute as monomer under the assay conditions and DARPins #19-23 and 27-30 are stable for at least 1 month at 40° C. in PBS (i.e. their elution profiles did not reveal any aggregation, multimerization or degradation tendency).

Example 3

Thermal Stability of DARPins with Binding Specificity of xSA

Thermal stability of DARPins with specificity for xSA was analyzed with a fluorescence-based thermal stability assay (Niesen, F. H., Nature Protocols 2(9): 2212-2221, 2007). Thereby, the temperature at which a protein (i.e. such a DARPin) unfolds is measured by an increase in the fluorescence of a dye (e.g. SYPRO orange; Invitrogen, cat. No. S6650) with affinity for hydrophobic parts of the protein, which are exposed as the protein unfolds. The temperature at the thereby obtained fluorescence transition midpoint (from lower fluorescence intensity to higher fluorescence intensity) then corresponds to the midpoint denaturation temperature (Tm) of the protein analyzed.

Fluorescence-based Thermal Stability Assay

Thermal denaturation of DARPins using SYPRO orange as a fluorescence dye was measured using a real time PCR instrument (i.e. the C1000 thermal cycler (BioRad) in combination with a CFX96 optical system (BioRad)). DARPins were prepared at 80 μM concentration in either PBS at pH 7.4 or MES buffer at pH 5.8 containing 1×SYPRO Orange (diluted from a 5'000×SYPRO Orange stock solution, Invitrogen) and 50 µl of such protein solutions or buffer only was added in a white 96-well PCR plate (Bio-Rad). The plates were sealed with Microseal 'B' Adhesive Seals (Bio-Rad) and heated in the real time PCR instrument from 20° C. to 95° C. in increments of 0.5° C. including a 25 sec hold step after each temperature increment, and the thermal denaturation of the DARPins was followed by measurement of the relative fluorescence units of the samples at each temperature increment. Relative fluorescence units in the wells of the plate were measured using channel 2 of the real time PCR instruments (i.e. excitation was at 515-535 nm and detection was at 560-580 nm), and the corresponding values obtained for buffer only were subtracted. From the thereby obtained thermal denaturation transition midpoints, Tm values for the analyzed DARPins can be determined.

The results of the thermal denaturation of DARPins in PBS at pH7.4 or MES-buffer at pH 5.8 followed by an increase in the fluorescence intensity of SYPRO Orange are shown in FIGS. 2A to 2D and FIGS. 3A and 3B. The measured thermal denaturation transitions demonstrate that all DARPins with binding specificity for xSA analyzed have Tm values well above 40° C. (at both pH 7.4 and pH 5.8).

Example 4

Characterization of the DARPins with Binding for Specificity for xSA by Surface Plasmon Resonance Analysis DARPins with binding specificity for xSA were immobilized in a flow cell via their His-tag to coated α-RGS-His antibody (Qiagen, cat. no. 34650), and the interaction of human, cynomolgus monkey (cyno), mouse, rat, rabbit and dog serum albumin with the immobilized DARPins were analyzed.

Surface Plasmon Resonance (SPR) Analysis

SPR was measured using a ProteOn instrument (BioRad) and measurement was performed according standard procedures known to the person skilled in the art. The running buffer was PBS, pH 7.4, containing 0.01% Tween 20®. Anti-RGS-His antibody was covalently immobilized on a GLC chip (BioRad) to a level of about 2000 resonance units (RU). Immobilization of DARPins on the antibody coated chip was then performed by injecting 150 µl of 1 µM DARPin solution in 300 s (flow rate=30 µl/min). The interaction with serum albumin of the different species was then measured by injecting in 60 sec a volume of 100 µl running buffer (PBS containing 0.01% Tween®) containing a distinct serum albumin at a concentration of 400, 200, 100, 50 nM (on-rate measurement), followed by a running buffer flow for 10 to 30 minutes (flow rate=100 µl/min) (off-rate measurement). The signals (i.e. resonance unit (RU) values) of an uncoated reference cell and a reference injection (i.e. injection of running buffer only) were subtracted from the RU traces obtained after injection of the serum albumins (double-referencing). From the SRP traces obtained from the on-rate and off-rate measurements the on- and off-rate of the corresponding DARPin serum albumin interaction can be determined.

The results are summarized in Table 1 and Table 2. Dissociation constants (Kd) were calculated from the estimated on- and off-rates using standard procedures known to the person skilled in the art and found to be in the range from about 3 to about 300 nM. While human and cynomolgus monkey serum albumin are bound by all DARPins analyzed, rabbit, mouse, rat and dog serum albumin is only bound by a subset of these DARPins.

TABLE 1

Dissociation constants of DARPin serum albumin interactions

| | Kd [nM] (human) | Kd [nM] (cyno) | Kd [nM] (mouse) | Kd [nM] (rat) | Kd [nM] (rabbit) | Kd [nM] (dog) |
|---|---|---|---|---|---|---|
| DARPin #29 | 15 | 7 | n.b. | n.b. | 17 | n.b. |
| DARPin #20 | 27 | 110 | 124 | 242 | n.b. | 185 |
| DARPin #27 | 11 | 6 | n.b. | n.b. | 19 | n.b. |
| DARPin #22 | 13 | 74 | 68 | 109 | n.b. | 81 |
| DARPin #28 | 6 | 3 | n.b. | n.b. | 9 | n.b. |
| DARPin #19 | 14 | 63 | 56 | 91 | n.b. | 77 |
| DARPin #21 | 26 | 110 | 142 | 266 | n.b. | 180 |
| DARPin #30 | 7 | 4 | n.b. | n.b. | 8 | n.b. |

Dissociation constants for various DARPin serum albumin (from different species as indicated in each column title) interactions were measured by using SPR. (n.b. = no binding observable).

TABLE 2

Dissociation constants of DARPin serum albumin interactions

| | Kd [nM] (human) |
|---|---|
| DARPin #43 | 30 |
| DARPin #44 | 39 |
| DARPin #45 | 35 |
| DARPin #46 | 43 |
| DARPin #47 | 96 |
| DARPin #48 | 68 |

Dissociation constants for various DARPin human serum albumin interactions were measured by using SPR.

Example 5

Terminal Plasma Half-Life of DARPins with Binding Specificity for xSA

The terminal plasma half-life of DARPins in mice and cynomolgus monkeys (Macaca fascicularis, also abbreviated as "cyno") was determined according to standard procedures known to the person skilled in the art (Toutain, et al., loc. cit.). A certain amount of DARPin was intravenously injected into a mammal and the DARPin clearance from the blood plasma was followed over time by following its plasma concentration. The DARPin concentration initially decreases until a pseudo-equilibrium is reached (alpha-phase) followed by an exponential further decrease of the DARPin concentration in the plasma (beta-phase). From this beta-phase the DARPin terminal plasma half-life can then be calculated.

Determination of the DARPin Plasma Clearance in Mice

In order to assess the plasma clearance of DARPins with binding specificity for xSA, the test proteins were radiolabeled and injected in the tail-vein of naïve Balb/c mice. The following DARPins were injected: DARPin#19, DARPin#21, DARPin #23, DARPin #25, DARPin #18, DARPin #32, DARPin #35, DARPin #36, DARPin #33, DARPin #34, DARPin #37, DARPin #38, DARPin #43, DARPin#44, DARPin#45, DARPin#46, DARPin#47 and DARPin#48. DARPins were radiolabeled with a $^{99m}$Tc-carbonyl complex as described previously (Weibel, R., et al., Nature Biotechnol. 17(9), 897-901, 1999). DARPins (40 μg) were incubated with $^{99m}$Tc-carbonyl (0.8-1.6 m Ci) for 1 h before being diluted to 400 μl in PBS (pH 7.4). Each mouse was injected intravenously with 100 μl of the thereby obtained labeled DARPin solution (equivalent to 10 μg protein and 0.2-0.4 m Ci). Blood samples of the mice were collected at 1 h, 4 h, 24 h, and 48 h after the initial injection and the radioactivity of the samples was measured. The level of radioactivity measured at a certain time point is a direct measure for the amount of DARPin still present in the blood plasma at that time point. The % injected dose is the percentage of the total radioactivity of the whole blood of the mouse (1.6 ml for a 18 g mouse) measured at a certain time point in relation to the total radioactivity of the injected sample corrected for the radioactive decay of $^{99m}$Tc.

DARPins with binding specificity for MSA have a strongly increased terminal plasma half-life in mice if compared to DARPin #32 having no binding specificity for xSA (FIGS. 4A and 4B). DARPin#19, DARPin#21, DARPin#23, DARPin#33, DARPin #37, DARPin #43, DARPin#44, DARPin#45, DARPin#46, DARPin#47 and DARPin#48 had a terminal plasma half-life in mice of about 2-2.5 days.

Determination of the DARPin Plasma Clearance in Cynomolgus Monkeys

DARPin diluted in PBS were injected as a bolus injection in the cephalic vein of cynomolgus monkeys. The following DARPins were injected: DARPin #26 (0.5 mg/kg), DARPin #24 (0.5 mg/kg), DARPin #17 (0.5 mg/kg), DARPin #34 (1 mg/kg), and DARPin #32 (0.5 mg/kg). At different time points after injection, plasma was generated from the blood collected from the femoral vein of the animals. The concentration of the DARPins in the plasma samples was then determined by a sandwich ELISA using standard protocols known to the person skilled in the art and an appropriate DARPin standard curve with known DARPin concentrations.

Plasma samples of cynomolgus monkeys were serially diluted in PBS-C (PBS containing 0.25% casein, pH 7.4) on MaxiSorp ELISA plates that were coated with an anti-DARPin specific rabbit monoclonal antibody. After extensive washing with PBS-T (PBS supplemented with 0.1% Tween 20®, pH 7.4) the plates were developed with the monoclonal anti-RGS(His)4 antibody labeled with horseradish peroxidase HRP (Qiagen). Binding was then detected by using 100 μl BM-Blue POD substrate (Roche Diagnostics). The reaction was stopped by adding 50 μl of 1 M $H_2SO_4$ and the absorbance at 450 nm (and subtracting the absorbance at 620 nm) was measured. The concentration of the DARPin in the plasma sample was calculated by performing a mono-exponential regression on a standard curve of the DARPin diluted in monkey serum (GraphPad Prism). The plasma terminal half-life of the DARPins was calculated by performing non-linear regressions (two-phase decay) on the determined concentration values up to 240 h after injection. The half-life of the second (beta) phase corresponds to the terminal plasma half-life.

DARPin with binding specificity for xSA have an increased terminal plasma half-life in cynomolgus monkey if compared to the DARPin #32 having no binding specificity for xSA (Table 3). DARPin#19, DARPin#21, DARPin #43, DARPin#44, DARPin#45, DARPin#46, DARPin#47 and DARPin#48 had a terminal plasma half-life in cynomolgus monkey of about 10 to 15 days.

TABLE 3

Estimations of terminal plasma half-life of DARPins in cynomolgus monkey (cyno)

|  | $t_{1/2}$ [h] |
| --- | --- |
| DARPin #32 | 0.2 |
| DARPin #26 | 129 |
| DARPin #34 | 111 |
| DARPin #17 | 40 |
| DARPin #24 | 126 |
| DARPin #19 | 288 |
| DARPin #21 | 384 |
| DARPin #28 | 144 |

Pharmacokinetic parameter estimates $t_{1/2}$: terminal plasma half-life

Example 6

Higher Thermal Stability of DARPins with Improved C-terminal Capping Modules

Thermal stability of DARPins was analyzed with a fluorescence-based thermal stability assay as described in Example 3. Alternatively, the thermal stability of a DARPin was analyzed by CD spectrometry; i.e. by measurement of its heat denaturation by following its circular dichroism (CD) signal at 222 nm by techniques well known to the person skilled in the art. The CD signal of the sample was recorded at 222 nm in a Jasco J-715 instrument (Jasco, Japan) while slowly heating the protein at a concentration of 0.02 mM in PBS pH 7.4 from 20° C. to 95° C. using a temperature ramp of 1° C. per min. This is an effective means to follow the denaturation of DARPins as they mainly consist of alpha helices that show a strong change in their CD signal at 222 nm upon unfolding. The midpoint of the observed transition of such a measured CD signal trace for a DARPin corresponds to its Tm value.

The thermal stability of DARPin #37 (SEQ ID NO:37 with a His-tag (SEQ ID NO:15) fused to its N-terminus) was compared to the thermal stability of DARPin #38 (SEQ ID NO:38 with a His-tag (SEQ ID NO:15) fused to its N-terminus) using the fluorescence-based thermal stability assay. These two DARPins posses an identical amino acid sequence except for the C-terminal capping module of their repeat domains. The repeat domain of DARPin #38, but not DARPin #37, comprises an improved C-capping module as described herein. The Tm values in PBS pH 7.4 determined for DARPin #37 and DARPin #38 were about 63° C. and about 73° C., respectively. The Tm values in MES buffer pH 5.8 determined for DARPin #37 and DARPin #38 were about 54.5° C. and about 66° C., respectively.

The thermal stability of DARPin #39 (SEQ ID NO:39 with a His-tag (SEQ ID NO:15) fused to its N-terminus) was compared to the thermal stability of DARPin #40 (SEQ ID NO:40 with a His-tag (SEQ ID NO:15) fused to its N-terminus) using the fluorescence-based thermal stability assay. These two DARPins posses an identical amino acid sequence except for the C-terminal capping module of their repeat domains. The repeat domain of DARPin #40, but not DARPin #39, comprises an improved C-capping module as described herein. The Tm values in MES buffer pH 5.8 determined for DARPin #39 and DARPin #40 were about 51° C. and about 55° C., respectively.

The thermal stability of DARPin #41 (SEQ ID NO:41) was compared to the thermal stability of DARPin #42 (SEQ ID NO:42) using CD spectroscopy. These two DARPins posses an identical amino acid sequence except for the C-terminal capping module of their repeat domains. The repeat domain of DARPin #42, but not DARPin #41, comprises an improved C-capping module as described herein. The Tm values in PBS pH 7.4 determined for DARPin #41 and DARPin #42 were about 59.5° C. and about 73° C., respectively.

The invention claimed is:

1. A method of increasing the terminal plasma half-life of a bioactive compound in a mammal, comprising covalently attaching a binding protein to said bioactive compound, wherein said binding protein comprises at least one ankyrin repeat domain, wherein said ankyrin repeat domain has binding specificity for a mammalian serum albumin, wherein said covalent attachment of said binding protein increases the terminal plasma half-life of said bioactive compound in a mammal at least 2-fold as compared to the terminal plasma half-life of said unmodified bioactive compound, and wherein said ankyrin repeat domain comprises an ankyrin repeat module having an amino acid sequence selected from the group consisting of:

(1) SEQ ID NO:49;
(2) SEQ ID NO:50;
(3) SEQ ID NO:51;
(4) SEQ ID NO:52;
(5) an amino acid sequence with up to 6 amino acids in SEQ ID NO: 49 exchanged by any amino acid and having the ankyrin repeat sequence motif (SEQ ID NO: 53)
X1DX2X3X4X5TPLHLAAX6X7GHLX8IVEVLLKX9GADVNA wherein
X1 represents an amino acid residue selected from the group consisting of A, D, M, F, S, I, T, N, Y, and K;
X2 represents an amino acid residue selected from the group consisting of E, K, D, F, M, N, I and Y;
X3 represents an amino acid residue selected from the group consisting of W, R, N, T, H, K, A and F;
X4 represents an amino acid residue selected from the group consisting of G and S;
X5 represents an amino acid residue selected from the group consisting of N, T and H;
X6 represents an amino acid residue selected from the group consisting of N, V and R;
X7 represents an amino acid residue selected from the group consisting of E, Y, N, D, H, S, A, Q, T and G;
X8 represent an amino acid residue selected from the group consisting of E and K;
X9 represent an amino acid residue selected from the group consisting of S, A, Y, H and N; and
wherein optionally up to 5 amino acids in other than in positions denoted with X in SEQ ID NO:53 are exchanged by any amino acid;
(6) an amino acid sequence with up to 6 amino acids in SEQ ID NO: 51 exchanged by any amino acid and having the ankyrin repeat sequence motif (SEQ ID NO: 10)
X1DX2X3GX4TPLHLAAX5X6GHLEIVEVLLKX7GADVNA wherein
X1 represents an amino acid residue selected from the group consisting of A, D, M, F, S, I, T, N, Y and K;
X2 represents an amino acid residue selected from the group consisting of E, K, D, F, M, N, I and Y;
X3 represents an amino acid residue selected from the group consisting of W, R, N, T, H, K, A and F;
X4 represents an amino acid residue selected from the group consisting of N, T and H;
X5 represents an amino acid residue selected from the group consisting of N, V and R;
X6 represents an amino acid residue selected from the group consisting of E, Y, N, D, H, S, A, Q, T and G;
X7 represent an amino acid residue selected from the group consisting of S, A, Y, H and N; and
wherein optionally up to 5 amino acids in other than in positions denoted with X in SEQ ID NO:10 are exchanged by any amino acid;
(7) an amino acid sequence with up to 6 amino acids in SEQ ID NO: 49 exchanged by any amino acid and having the ankyrin repeat sequence motif (SEQ ID NO: 11)
X1DYFX2HTPLHLAARX3X4HLX5IVEVLLKX6GADVNA wherein
X1 represents an amino acid residue selected from the group consisting of D, K and A;
X2 represents an amino acid residue selected from the group consisting of D, G and S;
X3 represents an amino acid residue selected from the group consisting of E, N, D, H, S, A, Q, T and G;
X4 represents an amino acid residue selected from the group consisting of G and D;
X5 represents an amino acid residue selected from the group consisting of E, K and G;
X6 represents an amino acid residue selected from the group consisting of H, Y, A and N; and
wherein optionally up to 5 amino acids in other than in positions denoted with X in SEQ ID NO:11 are exchanged by any amino acid;
(8) an amino acid sequence with up to 6 amino acids in SEQ ID NO: 50 exchanged by any amino acid and having the ankyrin repeat sequence motif (SEQ ID NO: 54)
X1DFX2GX3TPLHLAAX4X5GHLEIVEVLLKX6GADVNA wherein
X1 represents an amino acid residue selected from the group consisting of F, S, L and K;
X2 represents an amino acid residue selected from the group consisting of V and A;
X3 represents an amino acid residue selected from the group consisting of R and K;
X4 represents an amino acid residue selected from the group consisting of S and N;
X5 represents an amino acid residue selected from the group consisting N, D, Q, S, A, T and E;
X6 represents an amino acid residue selected from the group consisting of A, H, Y, S and N; and
wherein optionally up to 5 amino acids in other than in positions denoted with X in SEQ ID NO:54 are exchanged by any amino acid;
(9) an amino acid sequence with up to 6 amino acids in SEQ ID NO: 50 exchanged by any amino acid and has the ankyrin repeat sequence motif (SEQ ID NO: 12)
X1DFX2GX3TPLHLAAX4DGHLEIVEVLLKX5GADVNA wherein
X1 represents an amino acid residue selected from the group consisting of F, S, L and K;
X2 represents an amino acid residue selected from the group consisting of V and A;
X3 represents an amino acid residue selected from the group consisting of R and K;
X4 represents an amino acid residue selected from the group consisting of S and N;
X5 represents an amino acid residue selected from the group consisting of A, H, Y, S and N; and
wherein optionally up to 5 amino acids in other than in positions denoted with X in SEQ ID NO:12 are exchanged by any amino acid;
(10) an amino acid sequence with up to 6 amino acids in SEQ ID NO: 51 exchanged by any amino acid and has the ankyrin repeat sequence motif (SEQ ID NO: 13)
X1DX2X3GTTPLHLAAVYGHLEX4VEVLLKX5GADVNA wherein
X1 represents an amino acid residue selected from the group consisting of K, A, D, M, F, S, I, T, N, and Y;
X2 represents an amino acid residue selected from the group consisting of E, K, D, F, M, N and Y;
X3 represents an amino acid residue selected from the group consisting of R, N, T, H, K, A and F;
X4 represents an amino acid residue selected from the group consisting of I and M;
X5 represents an amino acid residue selected from the group consisting of H, Y, K, A and N; and
wherein optionally up to 5 amino acids in other than in positions denoted with X in SEQ ID NO:13 are exchanged by any amino acid; and
(11) an amino acid sequence with up to 6 amino acids in SEQ ID NO: 52 exchanged by any amino acid and has the ankyrin repeat sequence motif (SEQ ID NO: 14)
X1NETGYTPLHLADSSGHX2EIVEVLLKX3X4X5DX6NA wherein
X1 represents an amino acid residue selected from the group consisting of Q and K;
X2 represents an amino acid residue selected from the group consisting of L and P;
X3 represents an amino acid residue selected from the group consisting of H, N, Y and A;
X4 represents an amino acid residue selected from the group consisting of G and S;
X5 represents an amino acid residue selected from the group consisting of A, V, T and S;
X6 represents an amino acid residue selected from the group consisting of V and F; and
wherein optionally up to 5 amino acids in other than in positions denoted with X in SEQ ID NO:14 are exchanged by any amino acid.

2. A method of increasing the terminal plasma half-life of a bioactive compound in a mammal, comprising covalently attaching a binding protein to said bioactive compound, wherein said binding protein comprises at least one ankyrin repeat domain, wherein said ankyrin repeat domain has binding specificity for a mammalian serum albumin, wherein said covalent attachment of said binding protein increases the terminal plasma half-life of said bioactive compound in a mammal at least 2-fold as compared to the terminal plasma half-life of said unmodified bioactive compound, wherein said ankyrin repeat domain comprises an amino acid sequence that has at least 85% amino acid sequence identity with an ankyrin repeat domain selected from the group consisting of SEQ ID NOs: 17 to 31 and 43 to 48, wherein G at position 1 and/or S at position 2 of said ankyrin repeat domain are optionally missing.

3. A method of increasing the terminal plasma half-life of a bioactive compound in a mammal, comprising covalently attaching a binding protein to said bioactive compound, wherein said binding protein comprises at least one ankyrin repeat domain, wherein said ankyrin repeat domain has binding specificity for a mammalian serum albumin, wherein said covalent attachment of said binding protein increases the terminal plasma half-life of said bioactive compound in a mammal at least 2-fold as compared to the terminal plasma half-life of said unmodified bioactive compound, wherein said ankyrin repeat domain comprises an ankyrin repeat module having an amino acid sequence selected from the group consisting of:
(1) SEQ ID NO:49;
(2) SEQ ID NO:50;
(3) SEQ ID NO:51;
(4) SEQ ID NO:52;
(5) an amino acid sequence with up to 5 amino acids in SEQ ID NO: 49 exchanged by any amino acid;
(6) an amino acid sequence with up to 4 amino acids in SEQ ID NO: 50 exchanged by any amino acid;
(7) an amino acid sequence with up to 3 amino acids in SEQ ID NO: 51 exchanged by any amino acid; and
(8) an amino acid sequence with up to 6 amino acids in SEQ ID NO: 52 exchanged by any amino acid.

4. The method of claim 3, wherein said ankyrin repeat domain comprises an ankyrin repeat module having an amino acid sequence with up to 5 amino acids in SEQ ID NO: 49 exchanged by any amino acid.

5. The method of claim 3, wherein the terminal plasma half-life of the bioactive compound in mice is increased to about 2 to 2.5 days.

6. The method of claim 3, wherein the terminal plasma half-life of the bioactive compound in cynomolgus monkeys is increased to about 10 to 15 days.

7. The method of claim 3, wherein the bioactive compound is a proteinaceous bioactive compound.

8. The method of claim 7, wherein the proteinaceous bioactive compound is (1) a binding domain having binding specificity for a target different from mammalian serum albumin, (2) a cytokine, (3) a growth factor, (4) an antibody or a fragment thereof, or (5) a hormone.

9. The method of claim 3, wherein the bioactive compound is a nonproteinaceous bioactive compound.

10. The method of claim 9, wherein the non-proteinaceous bioactive compound is a toxin, a small molecule targeting GPCRs, or an antibiotic.

11. The method of claim 3, wherein said covalent attachment of said binding protein increases the terminal plasma half-life of the bioactive compound in a mammal at least 5-fold as compared to the terminal plasma half-life of said unmodified bioactive compound.

12. The method of claim 3, wherein said covalent attachment of said binding protein increases the terminal plasma half-life of the bioactive compound in a mammal at least 10-fold as compared to the terminal plasma half-life of said unmodified bioactive compound.

13. The method of claim 3, wherein the terminal plasma half-life of the binding protein in human is at least 5 days.

14. The method of claim 3, wherein the terminal plasma half-life of the binding protein in human is at least 10 days.

15. The method of claim 3, wherein said ankyrin repeat domain comprises an ankyrin repeat module having an amino acid sequence with up to 3 amino acids in SEQ ID NO: 49 exchanged by any amino acid.

16. The method of claim 3, wherein said ankyrin repeat domain comprises an ankyrin repeat module having the amino acid sequence of SEQ ID NO: 49.

17. The method of claim 3, wherein said ankyrin repeat domain comprises a first ankyrin repeat module having an amino acid sequence with up to 5 amino acids in SEQ ID NO: 49 exchanged by any amino acid and a second ankyrin repeat module having an amino acid sequence with up to 4 amino acids in SEQ ID NO: 50 exchanged by any amino acid, wherein said first ankyrin repeat module is N-terminal of said second ankyrin repeat module.

18. The method of claim 2, wherein said ankyrin repeat domain comprises an amino acid sequence that has at least 85% amino acid sequence identity with the ankyrin repeat domain of SEQ ID NO: 46, wherein G at position 1 and/or S at position 2 of said ankyrin repeat domain are optionally missing.

19. The method of claim 2, wherein said ankyrin repeat domain comprises an amino acid sequence that has at least 90% amino acid sequence identity with the ankyrin repeat domain of SEQ ID NO: 46, wherein G at position 1 and/or S at position 2 of said ankyrin repeat domain are optionally missing.

20. The method of claim 2, wherein said ankyrin repeat domain comprises an amino acid sequence that has at least 95% amino acid sequence identity with the ankyrin repeat domain of SEQ ID NO: 46, wherein G at position 1 and/or S at position 2 of said ankyrin repeat domain are optionally missing.

21. The method of claim 20, wherein the terminal plasma half-life of said ankyrin repeat domain in mice is about 2 to 2.5 days.

\* \* \* \* \*

UNITED STATES PATENT AND TRADEMARK OFFICE
CERTIFICATE OF CORRECTION

PATENT NO. : 9,775,912 B2
APPLICATION NO. : 15/013092
DATED : October 3, 2017
INVENTOR(S) : Daniel Steiner et al.

It is certified that error appears in the above-identified patent and that said Letters Patent is hereby corrected as shown below:

In the Claims

In Claim 1, Column 81, Line 57:
"X8 represent" should read --X8 represents--.

In Claim 1, Column 81, Line 59:
"X9 represent" should read --X9 represents--.

In Claim 1, Column 82, Line 16:
"$X_1DX_2X_3GX_4TPLHLAAX_5X_6GHLEIVEVLLKX_7GADVNA$" should read
--X1DX2X3GX4TPLHLAAX5X6GHLEIVEVLLKX7GADVNA--.

In Claim 1, Column 82, Line 31:
"X7 represent" should read --X7 represents--.

In Claim 1, Column 83, Line 11:
"group consisting N," should read --group consisting of N,--.

In Claim 9, Column 85, Line 9:
"nonproteinaceous" should read --non-proteinaceous--.

In Claim 13, Column 85, Line 23:
"in human" should read --in humans--.

In Claim 14, Column 85, Line 25:
"in human" should read --in humans--.

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*

```
                        SEQUENCE LISTING

<160> NUMBER OF SEQ ID NOS: 54

<210> SEQ ID NO 1
    <211> LENGTH: 32
    <212> TYPE: PRT
    <213> ORGANISM: Artificial Sequence
    <220> FEATURE:
    <223> OTHER INFORMATION: Synthetic Construct

<400> SEQUENCE: 1

Gly Ser Asp Leu Gly Lys Lys Leu Leu Glu Ala Ala Arg Ala Gly Gln
    1               5                   10                  15

Asp Asp Glu Val Arg Ile Leu Met Ala Asn Gly Ala Asp Val Asn Ala
                20                  25                  30

<210> SEQ ID NO 2
    <211> LENGTH: 28
    <212> TYPE: PRT
    <213> ORGANISM: Artificial Sequence
    <220> FEATURE:
    <223> OTHER INFORMATION: Synthetic Construct

<400> SEQUENCE: 2

Gln Asp Lys Phe Gly Lys Thr Ala Phe Asp Ile Ser Ile Asp Asn Gly
    1               5                   10                  15

Asn Glu Asp Leu Ala Glu Ile Leu Gln Lys Leu Asn
                20                  25

<210> SEQ ID NO 3
    <211> LENGTH: 28
    <212> TYPE: PRT
    <213> ORGANISM: Artificial Sequence
    <220> FEATURE:
    <223> OTHER INFORMATION: Synthetic Construct

<400> SEQUENCE: 3

Gln Asp Lys Phe Gly Lys Thr Pro Phe Asp Leu Ala Ile Arg Glu Gly
    1               5                   10                  15

His Glu Asp Ile Ala Glu Val Leu Gln Lys Ala Ala
                20                  25

<210> SEQ ID NO 4
    <211> LENGTH: 28
    <212> TYPE: PRT
    <213> ORGANISM: Artificial Sequence
    <220> FEATURE:
    <223> OTHER INFORMATION: Synthetic Construct

<400> SEQUENCE: 4

Gln Asp Lys Phe Gly Lys Thr Pro Phe Asp Leu Ala Ile Asp Asn Gly
    1               5                   10                  15

Asn Glu Asp Ile Ala Glu Val Leu Gln Lys Ala Ala
                20                  25

<210> SEQ ID NO 5
    <211> LENGTH: 30
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 5

Xaa Leu Xaa Lys Lys Leu Leu Glu Ala Ala Arg Ala Gly Gln Asp Asp
1               5                   10                  15

Glu Val Arg Ile Leu Xaa Ala Xaa Gly Ala Asp Val Asn Ala
            20                  25                  30

<210> SEQ ID NO 6
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 6

Xaa Asp Lys Xaa Gly Lys Thr Xaa Xaa Asp Xaa Xaa Xaa Asp Xaa Gly
1               5                   10                  15

Xaa Glu Asp Xaa Ala Glu Xaa Leu Gln Lys Ala Ala
            20                  25

<210> SEQ ID NO 7
```

```
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 7

Xaa Asp Lys Xaa Gly Lys Thr Xaa Ala Asp Xaa Xaa Xaa Asp Xaa Gly
1               5                  10                  15

Xaa Glu Asp Xaa Ala Glu Xaa Leu Gln Lys Ala Ala
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
```

```
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 8

Xaa Asp Lys Xaa Gly Lys Thr Xaa Ala Asp Xaa Xaa Ala Asp Xaa Gly
1               5                   10                  15

Xaa Glu Asp Xaa Ala Glu Xaa Leu Gln Lys Ala Ala
            20                  25

<210> SEQ ID NO 9
<211> LENGTH: 28
<212> TYPE: PRT
<213> ORGANISM: Artificial Sequence
<220> FEATURE:
<223> OTHER INFORMATION: Synthetic Construct

<400> SEQUENCE: 9

Gln Asp Lys Ser Gly Lys Thr Pro Ala Asp Leu Ala Ala Asp Ala Gly
1               5                   10                  15

His Glu Asp Ile Ala Glu Val Leu Gln Lys Ala Ala
            20                  25

<210> SEQ ID NO 10
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 10

Xaa Asp Xaa Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala

<210> SEQ ID NO 11
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
```

<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 11

Xaa Asp Tyr Phe Xaa His Thr Pro Leu His Leu Ala Ala Arg Xaa Xaa
1               5                   10                  15

His Leu Xaa Ile Val Glu Val Leu Leu Lys Xaa Gly Ala Asp Val Asn
            20                  25                  30

Ala

<210> SEQ ID NO 12
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 12

Xaa Asp Phe Xaa Gly Xaa Thr Pro Leu His Leu Ala Ala Xaa Asp Gly
1               5                   10                  15

His Leu Glu Ile Val Glu Val Leu Leu Lys Xaa Gly Ala Asp Val Asn
            20                  25                  30

Ala

<210> SEQ ID NO 13
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature

```
<222> LOCATION: (3)..(4)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 13

Xaa Asp Xaa Xaa Gly Thr Thr Pro Leu His Leu Ala Ala Val Tyr Gly
1               5                   10                  15

His Leu Glu Xaa Val Glu Val Leu Leu Lys Xaa Gly Ala Asp Val Asn
            20                  25                  30

Ala

<210> SEQ ID NO 14
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid

<400> SEQUENCE: 14

Xaa Asn Glu Thr Gly Tyr Thr Pro Leu His Leu Ala Asp Ser Ser Gly
1               5                   10                  15

His Xaa Glu Ile Val Glu Val Leu Leu Lys Xaa Xaa Xaa Asp Xaa Asn
            20                  25                  30

Ala

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Met Arg Gly Ser His His His His His His
1               5                   10

<210> SEQ ID NO 16
<211> LENGTH: 20
<212> TYPE: PRT
<213> ORGANISM: Artificial Sequence
<220> FEATURE:
<223> OTHER INFORMATION: Synthetic Construct

<400> SEQUENCE: 16

Gly Gly Gly Gly Ser Gly Gly Gly Gly Ser Gly Gly Gly Gly Ser Gly
```

-continued

```
1               5                   10                  15
Gly Gly Gly Ser
            20

<210> SEQ ID NO 17
<211> LENGTH: 126
<212> TYPE: PRT
<213> ORGANISM: Artificial Sequence
<220> FEATURE:
<223> OTHER INFORMATION: Synthetic Construct

<400> SEQUENCE: 17

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ala Asp Tyr Phe Gly His Thr Pro Leu His Leu Ala Ala Arg Asp Gly
        35                  40                  45

His Leu Lys Ile Val Glu Val Leu Leu Lys Tyr Gly Ala Asp Val Asn
    50                  55                  60

Ala Ser Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Leu Asn
        115                 120                 125

<210> SEQ ID NO 18
<211> LENGTH: 126
<212> TYPE: PRT
<213> ORGANISM: Artificial Sequence
<220> FEATURE:
<223> OTHER INFORMATION: Synthetic Construct

<400> SEQUENCE: 18

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ala Asp Tyr Phe Ser His Thr Pro Leu His Leu Ala Ala Arg Asp Gly
        35                  40                  45

His Leu Lys Ile Val Glu Val Leu Leu Lys Tyr Gly Ala Asp Val Asn
    50                  55                  60

Ala Ser Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Ala Phe Asp Ile Ser Ile Asp
            100                 105                 110

Asn Gly Asn Glu Asp Leu Ala Glu Ile Leu Gln Lys Leu Asn
        115                 120                 125

<210> SEQ ID NO 19
<211> LENGTH: 126
<212> TYPE: PRT
<213> ORGANISM: Artificial Sequence
<220> FEATURE:
```

<223> OTHER INFORMATION: Synthetic Construct

<400> SEQUENCE: 19

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
            85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Leu Asn
        115                 120                 125

<210> SEQ ID NO 20
<211> LENGTH: 126
<212> TYPE: PRT
<213> ORGANISM: Artificial Sequence
<220> FEATURE:
<223> OTHER INFORMATION: Synthetic Construct

<400> SEQUENCE: 20

Gly Ser Asp Leu Asp Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
            85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Leu Asn
        115                 120                 125

<210> SEQ ID NO 21
<211> LENGTH: 126
<212> TYPE: PRT
<213> ORGANISM: Artificial Sequence
<220> FEATURE:
<223> OTHER INFORMATION: Synthetic Construct

<400> SEQUENCE: 21

Gly Ser Asp Leu Asp Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Tyr Phe Ser His Thr Pro Leu His Leu Ala Ala Arg Asn Gly

```
            35                  40                  45

His Leu Glu Ile Val Glu Val Leu Lys Ala Gly Ala Asp Val Asn
 50                  55                  60

Ala Lys Asp Phe Ala Gly Lys Thr Pro Leu His Leu Ala Ala Asn Asp
 65                  70                  75                  80

Gly His Leu Glu Ile Val Glu Val Leu Leu Lys His Gly Ala Asp Val
                 85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Leu Asn
        115                 120                 125

<210> SEQ ID NO 22
<211> LENGTH: 126
<212> TYPE: PRT
<213> ORGANISM: Artificial Sequence
<220> FEATURE:
<223> OTHER INFORMATION: Synthetic Construct

<400> SEQUENCE: 22

Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                 20                  25                  30

Lys Asp Tyr Phe Ser His Thr Pro Leu His Leu Ala Ala Arg Asn Gly
             35                  40                  45

His Leu Glu Ile Val Glu Val Leu Leu Lys Ala Gly Ala Asp Val Asn
 50                  55                  60

Ala Lys Asp Phe Ala Gly Lys Thr Pro Leu His Leu Ala Ala Asn Asp
 65                  70                  75                  80

Gly His Leu Glu Ile Val Glu Val Leu Leu Lys His Gly Ala Asp Val
                 85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Leu Asn
        115                 120                 125

<210> SEQ ID NO 23
<211> LENGTH: 126
<212> TYPE: PRT
<213> ORGANISM: Artificial Sequence
<220> FEATURE:
<223> OTHER INFORMATION: Synthetic Construct

<400> SEQUENCE: 23

Gly Ser Asp Leu Gly Lys Lys Leu Leu Glu Ala Ala Arg Ala Gly Gln
 1               5                  10                  15

Asp Asp Glu Val Arg Ile Leu Leu Ala Ala Gly Ala Asp Val Asn Ala
                 20                  25                  30

Lys Asp Tyr Phe Ser His Thr Pro Leu His Leu Ala Ala Arg Asn Gly
             35                  40                  45

His Leu Lys Ile Val Glu Val Leu Leu Lys Ala Gly Ala Asp Val Asn
 50                  55                  60

Ala Lys Asp Phe Ala Gly Lys Thr Pro Leu His Leu Ala Ala Asn Asp
 65                  70                  75                  80

Gly His Leu Glu Ile Val Glu Val Leu Leu Lys His Gly Ala Asp Val
                 85                  90                  95
```

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Leu Asn
            115                 120                 125

<210> SEQ ID NO 24
<211> LENGTH: 126
<212> TYPE: PRT
<213> ORGANISM: Artificial Sequence
<220> FEATURE:
<223> OTHER INFORMATION: Synthetic Construct

<400> SEQUENCE: 24

Gly Ser Asp Leu Gly Lys Lys Leu Leu Glu Ala Ala Arg Ala Gly Gln
1               5                   10                  15

Asp Asp Glu Val Arg Ile Leu Met Ala Ser Gly Ala Asp Val Asn Ala
            20                  25                  30

Ala Asp Tyr Phe Ser His Thr Pro Leu His Leu Ala Ala Arg Asp Gly
        35                  40                  45

His Leu Lys Ile Val Glu Val Leu Leu Lys Tyr Gly Ala Asp Val Asp
    50                  55                  60

Ala Ser Asp Phe Ala Gly Lys Thr Pro Leu His Leu Ala Ala Asn Asp
65                  70                  75                  80

Gly His Leu Glu Ile Val Glu Val Leu Leu Lys His Asp Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Leu Asn
            115                 120                 125

<210> SEQ ID NO 25
<211> LENGTH: 126
<212> TYPE: PRT
<213> ORGANISM: Artificial Sequence
<220> FEATURE:
<223> OTHER INFORMATION: Synthetic Construct

<400> SEQUENCE: 25

Gly Ser Asp Leu Gly Lys Glu Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ala Asp Tyr Phe Gly His Thr Pro Leu His Leu Ala Ala Arg Asn Gly
        35                  40                  45

His Leu Lys Ile Val Glu Val Leu Leu Lys Tyr Gly Ala Asp Val Asn
    50                  55                  60

Ala Ser Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Ala Phe Glu Ile Ser Ile Asp
                100                 105                 110

Asn Gly Asn Glu Asp Leu Ala Glu Ile Leu Gln Lys Leu Asn
            115                 120                 125

<210> SEQ ID NO 26
<211> LENGTH: 126
<212> TYPE: PRT
<213> ORGANISM: Artificial Sequence

```
<220> FEATURE:
<223> OTHER INFORMATION: Synthetic Construct

<400> SEQUENCE: 26

Gly Ser Asp Leu Gly Lys Lys Leu Leu Glu Ala Ala Arg Ala Gly Gln
1               5                   10                  15

Asp Asp Glu Val Arg Phe Leu Met Ala Asn Gly Ala Asp Val Asn Ala
            20                  25                  30

Ala Asp Glu Arg Gly Thr Thr Pro Leu His Leu Ala Ala Val Tyr Gly
        35                  40                  45

His Leu Glu Ile Val Glu Val Leu Leu Lys Asn Gly Ala Asp Val Asn
    50                  55                  60

Ala Gln Asn Glu Thr Gly Tyr Thr Pro Leu His Leu Ala Asp Ser Ser
65                  70                  75                  80

Gly His Leu Glu Ile Val Glu Val Leu Leu Lys His Ser Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Leu Asn
        115                 120                 125

<210> SEQ ID NO 27
<211> LENGTH: 126
<212> TYPE: PRT
<213> ORGANISM: Artificial Sequence
<220> FEATURE:
<223> OTHER INFORMATION: Synthetic Construct

<400> SEQUENCE: 27

Gly Ser Asp Leu Asp Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Lys Asp Glu Arg Gly Thr Thr Pro Leu His Leu Ala Ala Val Tyr Gly
        35                  40                  45

His Leu Glu Ile Val Glu Val Leu Leu Lys Ala Gly Ala Asp Val Asn
    50                  55                  60

Ala Lys Asn Glu Thr Gly Tyr Thr Pro Leu His Leu Ala Asp Ser Ser
65                  70                  75                  80

Gly His Leu Glu Ile Val Glu Val Leu Leu Lys Ala Gly Ala Asp Val
                85                  90                  95

Asn Ala Gln Asp Lys Ser Gly Lys Thr Pro Ala Asp Leu Ala Ala Asp
            100                 105                 110

Ala Gly His Glu Asp Ile Ala Glu Val Leu Gln Lys Leu Asn
        115                 120                 125

<210> SEQ ID NO 28
<211> LENGTH: 126
<212> TYPE: PRT
<213> ORGANISM: Artificial Sequence
<220> FEATURE:
<223> OTHER INFORMATION: Synthetic Construct

<400> SEQUENCE: 28

Gly Ser Asp Leu Asp Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30
```

Lys Asp Glu Arg Gly Thr Thr Pro Leu His Leu Ala Ala Val Tyr Gly
                35                  40                  45

His Leu Glu Ile Val Glu Val Leu Leu Lys Ala Gly Ala Asp Val Asn
 50                  55                  60

Ala Lys Asn Glu Thr Gly Tyr Thr Pro Leu His Leu Ala Asp Ser Ser
 65                  70                  75                  80

Gly His Leu Glu Ile Val Glu Val Leu Leu Lys His Ser Ala Asp Val
                85                  90                  95

Asn Ala Gln Asp Lys Ser Gly Lys Thr Pro Ala Asp Leu Ala Ala Asp
                100                 105                 110

Ala Gly His Glu Asp Ile Ala Glu Val Leu Gln Lys Leu Asn
                115                 120                 125

<210> SEQ ID NO 29
<211> LENGTH: 126
<212> TYPE: PRT
<213> ORGANISM: Artificial Sequence
<220> FEATURE:
<223> OTHER INFORMATION: Synthetic Construct

<400> SEQUENCE: 29

Gly Ser Asp Leu Asp Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                20                  25                  30

Lys Asp Glu Arg Gly Thr Thr Pro Leu His Leu Ala Ala Val Tyr Gly
                35                  40                  45

His Leu Glu Ile Val Glu Val Leu Leu Lys Ala Gly Ala Asp Val Asn
 50                  55                  60

Ala Lys Asn Glu Thr Gly Tyr Thr Pro Leu His Leu Ala Asp Ser Ser
 65                  70                  75                  80

Gly His Leu Glu Ile Val Glu Val Leu Leu Lys His Gly Ala Asp Val
                85                  90                  95

Asn Ala Gln Asp Lys Ser Gly Lys Thr Pro Ala Asp Leu Ala Ala Asp
                100                 105                 110

Ala Gly His Glu Asp Ile Ala Glu Val Leu Gln Lys Leu Asn
                115                 120                 125

<210> SEQ ID NO 30
<211> LENGTH: 126
<212> TYPE: PRT
<213> ORGANISM: Artificial Sequence
<220> FEATURE:
<223> OTHER INFORMATION: Synthetic Construct

<400> SEQUENCE: 30

Gly Ser Asp Leu Asp Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                20                  25                  30

Lys Asp Glu Arg Gly Thr Thr Pro Leu His Leu Ala Ala Val Tyr Gly
                35                  40                  45

His Leu Glu Ile Val Glu Val Leu Leu Lys Ala Gly Ala Asp Val Asn
 50                  55                  60

Ala Lys Asn Glu Thr Gly Tyr Thr Pro Leu His Leu Ala Asp Ser Ser
 65                  70                  75                  80

Gly His Leu Glu Ile Val Glu Val Leu Leu Lys Ala Ser Ala Asp Val
                85                  90                  95

Asn Ala Gln Asp Lys Ser Gly Lys Thr Pro Ala Asp Leu Ala Ala Asp
                100                 105                 110

Ala Gly His Glu Asp Ile Ala Glu Val Leu Gln Lys Leu Asn
            115                 120                 125

<210> SEQ ID NO 31
<211> LENGTH: 157
<212> TYPE: PRT
<213> ORGANISM: Artificial Sequence
<220> FEATURE:
<223> OTHER INFORMATION: Synthetic Construct

<400> SEQUENCE: 31

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Val Asp Ile Trp Gly Asn Thr Pro Leu His Leu Ala Ala Asn Glu Gly
        35                  40                  45

His Leu Glu Ile Val Glu Val Leu Leu Lys His Gly Ala Asp Val Asn
    50                  55                  60

Ala Leu Asp His Trp Gly Asp Thr Pro Leu His Leu Ala Ala Met Trp
65                  70                  75                  80

Gly His Leu Glu Ile Val Glu Val Leu Leu Lys His Gly Ala Asp Val
                85                  90                  95

Asn Ala Leu Asp Asn Asn Gly Phe Thr Pro Leu His Leu Gly Tyr Gly
            100                 105                 110

His Leu Glu Ile Val Glu Val Leu Leu Lys His Gly Ala Asp Val Asn
        115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln Lys Leu Asn
145                 150                 155

<210> SEQ ID NO 32
<211> LENGTH: 126
<212> TYPE: PRT
<213> ORGANISM: Artificial Sequence
<220> FEATURE:
<223> OTHER INFORMATION: Synthetic Construct

<400> SEQUENCE: 32

Gly Ser Asp Leu Asp Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Arg Asp Ser Thr Gly Trp Thr Pro Leu His Leu Ala Ala Pro Trp Gly
        35                  40                  45

His Pro Glu Ile Val Glu Val Leu Leu Lys Asn Gly Ala Asp Val Asn
    50                  55                  60

Ala Ala Asp Phe Gln Gly Trp Thr Pro Leu His Leu Ala Ala Ala Val
65                  70                  75                  80

Gly His Leu Glu Ile Val Glu Val Leu Leu Lys Tyr Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Leu Asn

<210> SEQ ID NO 33
<211> LENGTH: 271
<212> TYPE: PRT
<213> ORGANISM: Artificial Sequence
<220> FEATURE:
<223> OTHER INFORMATION: Synthetic Construct

<400> SEQUENCE: 33

```
Gly Ser Asp Leu Gly Lys Lys Leu Leu Glu Ala Ala Arg Ala Gly Gln
1               5                   10                  15

Asp Asp Glu Val Arg Ile Leu Leu Ala Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Leu Gly Gly Gly
        115                 120                 125

Gly Ser Gly Gly Gly Gly Ser Gly Gly Gly Gly Ser Gly Gly Gly Gly
    130                 135                 140

Ser Arg Ser Asp Leu Gly Lys Lys Leu Leu Glu Ala Ala Arg Ala Gly
145                 150                 155                 160

Gln Asp Asp Glu Val Arg Ile Leu Met Ala Asn Gly Ala Asp Val Asn
                165                 170                 175

Ala Lys Asp Lys Asp Gly Tyr Thr Pro Leu His Leu Ala Ala Arg Glu
            180                 185                 190

Gly His Leu Glu Ile Val Glu Val Leu Leu Lys Ala Gly Ala Asp Val
        195                 200                 205

Asn Ala Lys Asp Lys Asp Gly Tyr Thr Pro Leu His Leu Ala Ala Arg
    210                 215                 220

Glu Gly His Leu Glu Ile Val Glu Val Leu Leu Lys Ala Gly Ala Asp
225                 230                 235                 240

Val Asn Ala Gln Asp Lys Phe Gly Lys Thr Ala Phe Asp Ile Ser Ile
                245                 250                 255

Asp Asn Gly Asn Glu Asp Leu Ala Glu Ile Leu Gln Lys Leu Asn
            260                 265                 270
```

<210> SEQ ID NO 34
<211> LENGTH: 271
<212> TYPE: PRT
<213> ORGANISM: Artificial Sequence
<220> FEATURE:
<223> OTHER INFORMATION: Synthetic Construct

<400> SEQUENCE: 34

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30
```

```
Ala Asp Tyr Phe Ser His Thr Pro Leu His Leu Ala Ala Arg Asn Gly
             35                  40                  45

His Leu Lys Ile Val Glu Val Leu Leu Lys Tyr Gly Ala Asp Val Asn
 50                  55                  60

Ala Ser Asp Phe Ala Gly Lys Thr Pro Leu His Leu Ala Ala Asn Asp
 65                  70                  75                  80

Gly His Leu Glu Ile Val Glu Val Leu Leu Lys His Gly Ala Asp Val
                 85                  90                  95

Asn Ala Gln Asp Ile Phe Gly Lys Thr Ala Phe Asp Ile Ser Ile Asp
                100                 105                 110

Asn Gly Asn Glu Asp Leu Ala Glu Ile Leu Gln Lys Leu Gly Gly Gly
                115                 120                 125

Gly Ser Gly Gly Gly Gly Ser Gly Gly Gly Gly Ser Gly Gly Gly Gly
    130                 135                 140

Ser Arg Ser Asp Leu Gly Lys Lys Leu Leu Glu Ala Ala Arg Ala Gly
145                 150                 155                 160

Gln Asp Asp Glu Val Arg Ile Leu Met Ala Asn Gly Ala Asp Val Asn
                165                 170                 175

Ala Lys Asp Lys Asp Gly Tyr Thr Pro Leu His Leu Ala Ala Arg Glu
                180                 185                 190

Gly His Leu Glu Ile Val Glu Val Leu Leu Lys Ala Gly Ala Asp Val
                195                 200                 205

Asn Ala Lys Asp Lys Asp Gly Tyr Thr Pro Leu His Leu Ala Ala Arg
                210                 215                 220

Glu Gly His Leu Glu Ile Val Glu Val Leu Leu Lys Ala Gly Ala Asp
225                 230                 235                 240

Val Asn Ala Gln Asp Lys Phe Gly Lys Thr Ala Phe Asp Ile Ser Ile
                245                 250                 255

Asp Asn Gly Asn Glu Asp Leu Ala Glu Ile Leu Gln Lys Leu Asn
                260                 265                 270
```

<210> SEQ ID NO 35
<211> LENGTH: 271
<212> TYPE: PRT
<213> ORGANISM: Artificial Sequence
<220> FEATURE:
<223> OTHER INFORMATION: Synthetic Construct

<400> SEQUENCE: 35

```
Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                 20                  25                  30

Lys Asp Lys Asp Gly Tyr Thr Pro Leu His Leu Ala Ala Arg Glu Gly
                 35                  40                  45

His Leu Glu Ile Val Glu Val Leu Leu Lys Ala Gly Ala Asp Val Asn
 50                  55                  60

Ala Lys Asp Lys Asp Gly Tyr Thr Pro Leu His Leu Ala Ala Arg Glu
 65                  70                  75                  80

Gly His Leu Glu Ile Val Glu Val Leu Leu Lys Ala Gly Ala Asp Val
                 85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Leu Gly Gly Gly
                115                 120                 125
```

Gly Ser Gly Gly Gly Gly Ser Gly Gly Gly Ser Gly Gly Gly
    130                 135                 140

Ser Arg Ser Asp Leu Gly Lys Lys Leu Leu Glu Ala Ala Arg Ala Gly
145                 150                 155                 160

Gln Asp Asp Glu Val Arg Ile Leu Leu Ala Ala Gly Ala Asp Val Asn
                165                 170                 175

Ala Lys Asp Tyr Phe Ser His Thr Pro Leu His Leu Ala Ala Arg Asn
                180                 185                 190

Gly His Leu Lys Ile Val Glu Val Leu Leu Lys Ala Gly Ala Asp Val
                195                 200                 205

Asn Ala Lys Asp Phe Ala Gly Lys Thr Pro Leu His Leu Ala Ala Asn
210                 215                 220

Asp Gly His Leu Glu Ile Val Glu Val Leu Leu Lys His Gly Ala Asp
225                 230                 235                 240

Val Asn Ala Gln Asp Ile Phe Gly Lys Thr Pro Ala Asp Ile Ala Ala
                245                 250                 255

Asp Ala Gly His Glu Asp Ile Ala Glu Val Leu Gln Lys Leu Asn
                260                 265                 270

<210> SEQ ID NO 36
<211> LENGTH: 302
<212> TYPE: PRT
<213> ORGANISM: Artificial Sequence
<220> FEATURE:
<223> OTHER INFORMATION: Synthetic Construct

<400> SEQUENCE: 36

Gly Ser Asp Leu Asp Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Arg Asp Ser Thr Gly Trp Thr Pro Leu His Leu Ala Ala Pro Trp Gly
            35                  40                  45

His Pro Glu Ile Val Glu Val Leu Leu Lys Asn Gly Ala Asp Val Asn
    50                  55                  60

Ala Ala Asp Phe Gln Gly Trp Thr Pro Leu His Leu Ala Ala Val
65                  70                  75                  80

Gly His Leu Glu Ile Val Glu Val Leu Leu Lys Tyr Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Leu Gly Gly Gly
                115                 120                 125

Gly Ser Gly Gly Gly Gly Ser Gly Gly Gly Ser Gly Gly Gly Gly
    130                 135                 140

Ser Arg Ser Asp Leu Gly Lys Lys Leu Leu Glu Ala Ala Arg Ala Gly
145                 150                 155                 160

Gln Asp Asp Glu Val Arg Ile Leu Met Ala Asn Gly Ala Asp Val Asn
                165                 170                 175

Ala Val Asp Ile Trp Gly Asn Thr Pro Leu His Leu Ala Ala Asn Glu
            180                 185                 190

Gly His Leu Glu Ile Val Glu Val Leu Leu Lys His Gly Ala Asp Val
                195                 200                 205

Asn Ala Leu Asp His Trp Gly Asp Thr Pro Leu His Leu Ala Ala Met
    210                 215                 220

```
Trp Gly His Leu Glu Ile Val Glu Val Leu Lys His Gly Ala Asp
225                 230                 235                 240

Val Asn Ala Leu Asp Asn Asn Gly Phe Thr Pro Leu His Leu Gly Tyr
            245                 250                 255

Gly His Leu Glu Ile Val Glu Val Leu Leu Lys His Gly Ala Asp Val
        260                 265                 270

Asn Ala Gln Asp Lys Phe Gly Lys Thr Ala Phe Asp Ile Ser Ile Asp
        275                 280                 285

Asn Gly Asn Glu Asp Leu Ala Glu Ile Leu Gln Lys Leu Asn
        290                 295                 300
```

<210> SEQ ID NO 37
<211> LENGTH: 126
<212> TYPE: PRT
<213> ORGANISM: Artificial Sequence
<220> FEATURE:
<223> OTHER INFORMATION: Synthetic Construct

<400> SEQUENCE: 37

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ala Asp Tyr Phe Ser His Thr Pro Leu His Leu Ala Ala Arg Asn Gly
        35                  40                  45

His Leu Lys Ile Val Glu Val Leu Leu Lys Tyr Gly Ala Asp Val Asn
    50                  55                  60

Ala Ser Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Ala Phe Asp Ile Ser Ile Asp
            100                 105                 110

Asn Gly Asn Glu Asp Leu Ala Glu Ile Leu Gln Lys Leu Asn
        115                 120                 125
```

<210> SEQ ID NO 38
<211> LENGTH: 126
<212> TYPE: PRT
<213> ORGANISM: Artificial Sequence
<220> FEATURE:
<223> OTHER INFORMATION: Synthetic Construct

<400> SEQUENCE: 38

```
Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
            20                  25                  30

Ala Asp Tyr Phe Ser His Thr Pro Leu His Leu Ala Ala Arg Asn Gly
        35                  40                  45

His Leu Lys Ile Val Glu Val Leu Leu Lys Tyr Gly Ala Asp Val Asn
    50                  55                  60

Ala Ser Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Pro Ala Asp Ile Ala Ala Asp
            100                 105                 110
```

Asn Gly His Glu Asp Ile Ala Glu Val Leu Gln Lys Leu Asn
        115                 120                 125

<210> SEQ ID NO 39
<211> LENGTH: 126
<212> TYPE: PRT
<213> ORGANISM: Artificial Sequence
<220> FEATURE:
<223> OTHER INFORMATION: Synthetic Construct

<400> SEQUENCE: 39

Gly Ser Asp Leu Gly Lys Lys Leu Leu Glu Ala Ala Arg Ala Gly Gln
1               5                   10                  15

Asp Asp Glu Val Arg Ile Leu Leu Ala Ala Gly Ala Asp Val Asn Ala
            20                  25                  30

Ala Asp Glu Arg Gly Thr Thr Pro Leu His Leu Ala Ala Val Tyr Gly
        35                  40                  45

His Leu Glu Ile Val Glu Val Leu Leu Lys Asn Gly Ala Asp Val Asn
    50                  55                  60

Ala Gln Asn Glu Thr Gly Tyr Thr Pro Leu His Leu Ala Asp Ser Ser
65                  70                  75                  80

Gly His Leu Glu Ile Val Glu Val Leu Leu Lys His Ser Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Leu Asn
        115                 120                 125

<210> SEQ ID NO 40
<211> LENGTH: 126
<212> TYPE: PRT
<213> ORGANISM: Artificial Sequence
<220> FEATURE:
<223> OTHER INFORMATION: Synthetic Construct

<400> SEQUENCE: 40

Gly Ser Asp Leu Gly Lys Lys Leu Leu Glu Ala Ala Arg Ala Gly Gln
1               5                   10                  15

Asp Asp Glu Val Arg Ile Leu Leu Ala Ala Gly Ala Asp Val Asn Ala
            20                  25                  30

Ala Asp Glu Arg Gly Thr Thr Pro Leu His Leu Ala Ala Val Tyr Gly
        35                  40                  45

His Leu Glu Ile Val Glu Val Leu Leu Lys Asn Gly Ala Asp Val Asn
    50                  55                  60

Ala Gln Asn Glu Thr Gly Tyr Thr Pro Leu His Leu Ala Asp Ser Ser
65                  70                  75                  80

Gly His Leu Glu Ile Val Glu Val Leu Leu Lys His Ser Ala Asp Val
                85                  90                  95

Asn Ala Gln Asp Lys Ser Gly Lys Thr Pro Ala Asp Ile Ala Ala Asp
            100                 105                 110

Asn Gly His Glu Asp Ile Ala Glu Val Leu Gln Lys Leu Asn
        115                 120                 125

<210> SEQ ID NO 41
<211> LENGTH: 103
<212> TYPE: PRT
<213> ORGANISM: Artificial Sequence
<220> FEATURE:
<223> OTHER INFORMATION: Synthetic Construct

<400> SEQUENCE: 41

Met Arg Gly Ser His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Phe Gly
65                  70                  75                  80

Lys Thr Ala Phe Asp Ile Ser Ile Asp Asn Gly Asn Glu Asp Leu Ala
                85                  90                  95

Glu Ile Leu Gln Lys Leu Asn
            100

<210> SEQ ID NO 42
<211> LENGTH: 103
<212> TYPE: PRT
<213> ORGANISM: Artificial Sequence
<220> FEATURE:
<223> OTHER INFORMATION: Synthetic Construct

<400> SEQUENCE: 42

Met Arg Gly Ser His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Lys Asp Lys Asp Gly Tyr
        35                  40                  45

Thr Pro Leu His Leu Ala Ala Arg Glu Gly His Leu Glu Ile Val Glu
    50                  55                  60

Val Leu Leu Lys Ala Gly Ala Asp Val Asn Ala Gln Asp Lys Ser Gly
65                  70                  75                  80

Lys Thr Pro Ala Asp Leu Ala Ala Asp Asn Gly His Glu Asp Ile Ala
                85                  90                  95

Glu Val Leu Gln Lys Ala Ala
            100

<210> SEQ ID NO 43
<211> LENGTH: 126
<212> TYPE: PRT
<213> ORGANISM: Artificial Sequence
<220> FEATURE:
<223> OTHER INFORMATION: Synthetic Construct

<400> SEQUENCE: 43

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Leu Asn
            115                 120                 125

<210> SEQ ID NO 44
<211> LENGTH: 126
<212> TYPE: PRT
<213> ORGANISM: Artificial Sequence
<220> FEATURE:
<223> OTHER INFORMATION: Synthetic Construct

<400> SEQUENCE: 44

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
                20                  25                  30

Lys Asp Tyr Phe Ser His Thr Pro Leu His Leu Ala Ala Arg Asn Gly
            35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys His Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Leu Asn
            115                 120                 125

<210> SEQ ID NO 45
<211> LENGTH: 126
<212> TYPE: PRT
<213> ORGANISM: Artificial Sequence
<220> FEATURE:
<223> OTHER INFORMATION: Synthetic Construct

<400> SEQUENCE: 45

Gly Ser Asp Leu Gly Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
                20                  25                  30

Lys Asp Tyr Phe Ser His Thr Pro Leu His Leu Ala Ala Arg Asn Gly
            35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
                100                 105                 110

Ala Gly His Glu Asp Ile Ala Glu Val Leu Gln Lys Leu Asn
            115                 120                 125

<210> SEQ ID NO 46
<211> LENGTH: 126
<212> TYPE: PRT
<213> ORGANISM: Artificial Sequence
<220> FEATURE:
<223> OTHER INFORMATION: Synthetic Construct

<400> SEQUENCE: 46

Gly Ser Asp Leu Gly Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Leu Asn
        115                 120                 125

<210> SEQ ID NO 47
<211> LENGTH: 126
<212> TYPE: PRT
<213> ORGANISM: Artificial Sequence
<220> FEATURE:
<223> OTHER INFORMATION: Synthetic Construct

<400> SEQUENCE: 47

Gly Ser Asp Leu Asp Lys Lys Leu Leu Glu Ala Ala Arg Ala Gly Gln
1               5                   10                  15

Asp Asp Glu Val Arg Ile Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Leu Asn
        115                 120                 125

<210> SEQ ID NO 48
<211> LENGTH: 126
<212> TYPE: PRT
<213> ORGANISM: Artificial Sequence
<220> FEATURE:
<223> OTHER INFORMATION: Synthetic Construct

<400> SEQUENCE: 48

Gly Ser Asp Leu Asp Lys Lys Leu Leu Glu Ala Ala Arg Ala Gly Gln
1               5                   10                  15

Asp Asp Glu Val Arg Glu Leu Leu Lys Ala Gly Ala Asp Val Asn Ala
            20                  25                  30

Lys Asp Tyr Phe Ser His Thr Pro Leu His Leu Ala Ala Arg Asn Gly
        35                  40                  45

His Leu Lys Ile Val Glu Val Leu Leu Lys Ala Gly Ala Asp Val Asn
    50                  55                  60

Ala Lys Asp Phe Ala Gly Lys Thr Pro Leu His Leu Ala Ala Asn Asp
65                  70                  75                  80

Gly His Leu Glu Ile Val Glu Val Leu Leu Lys Ala Gly Ala Asp Val
                85                  90                  95

Asn Ala Gln Asp Ile Phe Gly Lys Thr Pro Ala Asp Ile Ala Ala Asp
            100                 105                 110

Ala Gly His Glu Asp Ile Ala Glu Val Leu Gln Lys Leu Asn
        115                 120                 125

<210> SEQ ID NO 49
<211> LENGTH: 33
<212> TYPE: PRT
<213> ORGANISM: Artificial Sequence
<220> FEATURE:
<223> OTHER INFORMATION: Synthetic Construct

<400> SEQUENCE: 49

Lys Asp Tyr Phe Ser His Thr Pro Leu His Leu Ala Ala Arg Asn Gly
1               5                   10                  15

His Leu Lys Ile Val Glu Val Leu Leu Lys Ala Gly Ala Asp Val Asn
            20                  25                  30

Ala

<210> SEQ ID NO 50
<211> LENGTH: 33
<212> TYPE: PRT
<213> ORGANISM: Artificial Sequence
<220> FEATURE:
<223> OTHER INFORMATION: Synthetic Construct

<400> SEQUENCE: 50

Lys Asp Phe Ala Gly Lys Thr Pro Leu His Leu Ala Ala Asn Asp Gly
1               5                   10                  15

His Leu Glu Ile Val Glu Val Leu Leu Lys Ala Gly Ala Asp Val Asn
            20                  25                  30

Ala

<210> SEQ ID NO 51
<211> LENGTH: 33
<212> TYPE: PRT
<213> ORGANISM: Artificial Sequence
<220> FEATURE:
<223> OTHER INFORMATION: Synthetic Construct

<400> SEQUENCE: 51

Lys Asp Glu Arg Gly Thr Thr Pro Leu His Leu Ala Ala Val Tyr Gly
1               5                   10                  15

His Leu Glu Ile Val Glu Val Leu Leu Lys Ala Gly Ala Asp Val Asn
            20                  25                  30

Ala

<210> SEQ ID NO 52
<211> LENGTH: 33

```
<212> TYPE: PRT
<213> ORGANISM: Artificial Sequence
<220> FEATURE:
<223> OTHER INFORMATION: Synthetic Construct

<400> SEQUENCE: 52

Lys Asn Glu Thr Gly Tyr Thr Pro Leu His Leu Ala Asp Ser Ser Gly
1               5                   10                  15

His Leu Glu Ile Val Glu Val Leu Leu Lys His Ser Ala Asp Val Asn
            20                  25                  30

Ala

<210> SEQ ID NO 53
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 53

Xaa Asp Xaa Xaa Xaa Xaa Thr Pro Leu His Leu Ala Ala Xaa Xaa Gly
1               5                   10                  15

His Leu Xaa Ile Val Glu Val Leu Leu Lys Xaa Gly Ala Asp Val Asn
            20                  25                  30

Ala

<210> SEQ ID NO 54
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (27)..(27)
```

-continued

<223> OTHER INFORMATION: Xaa can be any naturally occurring amino acid

<400> SEQUENCE: 54

Xaa Asp Phe Xaa Gly Xaa Thr Pro Leu His Leu Ala Ala Xaa Xaa Gly
1               5                   10                  15

His Leu Glu Ile Val Glu Val Leu Leu Lys Xaa Gly Ala Asp Val Asn
            20                  25                  30

Ala